(12) United States Patent
Yokouchi et al.

(10) Patent No.: US 11,887,293 B2
(45) Date of Patent: Jan. 30, 2024

(54) MEDICINE VERIFICATION DEVICE AND BOUNDARY RECESS DETECTION METHOD

(71) Applicant: FUJIFILM Toyama Chemical Co., Ltd., Tokyo (JP)

(72) Inventors: Koji Yokouchi, Ashigarakami-gun (JP); Kazuchika Iwami, Ashigarakami-gun (JP)

(73) Assignee: FUJIFILM TOYAMA CHEMICAL CO., LTD., Tokyo (JP)

( * ) Notice: Subject to any disclaimer, the term of this patent is extended or adjusted under 35 U.S.C. 154(b) by 813 days.

(21) Appl. No.: 17/006,414

(22) Filed: Aug. 28, 2020

(65) Prior Publication Data

US 2020/0394786 A1 Dec. 17, 2020

Related U.S. Application Data

(63) Continuation of application No. PCT/JP2019/002942, filed on Jan. 29, 2019.

(30) Foreign Application Priority Data

Mar. 26, 2018 (JP) .................................. 2018-058105

(51) Int. Cl.
*G06T 7/00* (2017.01)
*G16H 20/13* (2018.01)
(Continued)

(52) U.S. Cl.
CPC ............ *G06T 7/0004* (2013.01); *A61J 7/0076* (2013.01); *B65B 57/14* (2013.01); *G06T 7/97* (2017.01);
(Continued)

(58) Field of Classification Search
CPC ...................... G06T 7/0004; G06T 7/97; G06T 2207/10028; G06T 2207/10152;
(Continued)

(56) References Cited

U.S. PATENT DOCUMENTS 6,212,855 B1 * 4/2001 Yasunaga ................ B65B 63/06
53/119
6,330,351 B1 * 12/2001 Yasunaga ............... G06V 20/66
235/375
(Continued)

FOREIGN PATENT DOCUMENTS

EP 3192486 A2 7/2017
JP 2006-69618 A 3/2006
(Continued)

OTHER PUBLICATIONS

Japanese Office Action for corresponding Japanese Application No. 2020-509743, dated Jun. 21, 2022, with English translation.

(Continued)

*Primary Examiner* — Roy M Punnoose
(74) *Attorney, Agent, or Firm* — Birch, Stewart, Kolasch & Birch, LLP

(57) ABSTRACT

A medicine verification device of the present invention includes: a detection unit that detects a boundary recess formed at a boundary position between a plurality of packaging bags each of which packs a medicine and is connected to form a continuous packaging bag having a strip-like shape; and an image capturing unit that captures an image of a surface of an imaging target portion on which at least the boundary recess is located a plurality of times while imaging conditions are changed in a state where light is emitted toward the surface of the imaging target portion in the continuous packaging bag, wherein the detection unit detects the boundary recess in the imaging target portion on the basis of the plurality of images captured while changing the imaging conditions by the image capturing unit.

18 Claims, 14 Drawing Sheets

(51) Int. Cl.
*A61J 7/00* (2006.01)
*B65B 57/14* (2006.01)
*G06V 10/141* (2022.01)
*B65B 9/087* (2012.01)

(52) U.S. Cl.
CPC .......... *G06V 10/141* (2022.01); *G16H 20/13* (2018.01); *B65B 9/087* (2013.01)

(58) Field of Classification Search
CPC ........ G06T 7/586; A61J 7/0076; B65B 57/14; B65B 9/087; B65B 9/06; G06V 10/141; G16H 20/13; G16H 20/10; G16H 40/20; G01N 21/9508; G06Q 50/04; Y02P 90/30
See application file for complete search history.

(56) References Cited

U.S. PATENT DOCUMENTS

| | | | | |
|---|---|---|---|---|
| 8,340,392 | B2* | 12/2012 | Kim ........................ | G01B 11/24 700/109 |
| 9,233,767 | B2* | 1/2016 | Amano .................... | B65B 57/10 |
| 9,272,796 | B1* | 3/2016 | Chudy ................. | G01N 21/9508 |
| 10,435,192 | B2* | 10/2019 | Luciano, Jr. ............ | B65B 57/10 |
| 10,594,956 | B2* | 3/2020 | Holmes ................... | H04N 23/11 |
| 2006/0213816 | A1* | 9/2006 | Jorritsma ............... | G06V 20/66 209/576 |
| 2006/0271237 | A1* | 11/2006 | Kim ........................ | G06V 20/66 700/226 |
| 2007/0150092 | A1* | 6/2007 | Ohmura ................. | G07F 7/1025 700/231 |
| 2010/0170206 | A1* | 7/2010 | Kim ........................ | B65B 61/28 53/525 |
| 2012/0216485 | A1* | 8/2012 | Amano ............... | G07F 17/0092 53/64 |
| 2013/0170732 | A1* | 7/2013 | Gotou ................. | G01N 21/9508 382/141 |
| 2013/0264376 | A1* | 10/2013 | Kim ........................ | B65B 63/04 229/87.05 |
| 2013/0342676 | A1* | 12/2013 | Amano ................... | G07F 9/026 348/86 |
| 2015/0266604 | A1 | 9/2015 | Amano et al. | |
| 2015/0355104 | A1 | 12/2015 | Matsuda | |
| 2016/0114925 | A1* | 4/2016 | Yuyama ................. | G16H 30/20 382/141 |

FOREIGN PATENT DOCUMENTS

| | | | |
|---|---|---|---|
| JP | 2008-334062 | A | 12/2006 |
| JP | 2007-68845 | A | 3/2007 |
| JP | 5196285 | B1 | 5/2013 |
| JP | 2013-144101 | A | 7/2013 |
| JP | 2015-232486 | A | 12/2015 |
| JP | 2017-47975 | A | 3/2017 |
| JP | 2017-90194 | A | 5/2017 |
| JP | 2017-90360 | A | 5/2017 |
| JP | 2017-207356 | A | 11/2017 |
| JP | 2018-20247 | A | 2/2018 |
| WO | WO 2014/129526 | A1 | 8/2014 |

OTHER PUBLICATIONS

Japanese Notice of Reasons for Refusal for Japanese Application No. 2020-509743, dated Jun. 8, 2021, with an English translation.
English translation of the International Search Report (form PCT/ISA/210), dated Mar. 19, 2019, for International Application No. PCT/JP2019/002942.
Written Opinion of the International Searching Authority (form PCT/ISA/237), dated Mar. 19, 2019, for International Application No. PCT/JP2019/002942, with an English translation.
Antensteiner et al., "High-Precision 3D Sensing with Hybrid Light Field & Photometric Stereo Approach in Multi-Line Scan Framework," IS&T International Symposium on Electronic Imaging, Intelligent Robotics and Industrial Applications using Computer Vision, 2017, pp. 52-60.
Extended European Search Report for European Application No. 19775083.9, dated May 10, 2021.
Farooq et al., "Dynamic photometric stereo for on line quality control of ceramic tiles," Computers in Industry, vol. 56, 2005 (published online Oct. 10, 2005), pp. 918-934.
Japanese Office Action for corresponding Japanese Application No. 2020-509743, dated Dec. 21, 2021, with English translation.

* cited by examiner

| TYPE | NAME | IDENTIFICATION INFORMATION | PLAN VIEW SIZE | THICKNESS | MASTER IMAGE |
|---|---|---|---|---|---|
| F1 | NAME F1 | AX | S1(mm) | h1(mm) | AX |
| F2 | NAME F2 | BW | S2(mm) | h2(mm) | BW |
| F3 | NAME F3 | T | S3(mm) | h3(mm) | T |
| ⋮ | | | | | |

DB

MEDICINE VERIFICATION DEVICE AND BOUNDARY RECESS DETECTION METHOD

CROSS-REFERENCE TO RELATED APPLICATIONS

This application is a Continuation of PCT International Application No. PCT/JP2019/002942 filed on Jan. 29, 2019, which claims priority under 35 U.S.C. § 119(a) to Japanese Patent Application No. 2018-058105 filed on Mar. 26, 2018. The above application is hereby expressly incorporated by reference, in its entirety, into the present application.

BACKGROUND OF THE INVENTION

The present invention relates to a medicine verification device and a boundary recess detection method, and more particularly relates to a medicine verification device and a boundary recess detection method adapted to detect boundary recess formed at a boundary position between a plurality of packaging bags each of which packs a medicine and is connected to form a continuous packaging bag having a strip-like shape.

As an already known technique, an automatic verification (inspection) has been performed by a machine or the like as to whether a medicine is correctly packaged in a packaging bag such as a sachet sheet as instructed by a prescription. Such an automatic inspection device (hereinafter, referred to as a medicine verification device) captures an image of a medicine packed in a packaging bag, for example, within the device. The device then performs verification as to whether the type and number of medicines appearing in the captured image match the type and number of medicines on which an instruction is given in the prescription.

Meanwhile, there are cases where a plurality of packaging bags each containing medicines are continuously connected in a strip-like shape to form a continuous member (hereinafter referred to as a continuous packaging bag). Some of the medicine verification devices described above introduce a continuous packaging bag into the device and verify the suitability of the medicine for each of the packaging bags targeting the medicines packed in each of the packaging bags of the continuous packaging bag. In the case of individually performing verification on each of the packaging bags of the continuous packaging bag, there is a need to define a region for one packaging bag on the captured image. For that purpose, it is important to detect an end position of the packaging bag, in other words, a boundary position between the packaging bags in the continuous packaging bag. The boundary position between the packaging bags usually has a boundary recess in the form of a cutout line or the like. Unfortunately, however, the boundary recess is relatively small and easily flattened. Therefore, the boundary recess in an image cannot be clearly confirmed, making it difficult to improve the probability and accuracy in detection of the recess. Under such circumstances, there have been methods, in recent years, being developed for specifying the end position of the packaging bag without directly detecting the boundary recess (for example, refer to JP 2006-334062 A (Patent Literature 1), JP 2017-47975 A (Patent Literature 2), JP 2013-144101 A (Patent Literature 3), and JP 5196285 B2 (Patent Literature 4).

The technique described in Patent Literature 1 relates to a tablet counting checking device (corresponding to a medicine verification device) that sequentially transfers a sachet sheet (corresponding to a continuous packaging bag) including a series of packages (corresponding to a packaging bag) formed by heat sealing, images the package using an illumination device and an imaging device disposed to face each other on both sides of an imaging range on the transfer path, extracts a medicine image region from the captured image, and counts the medicine images in the extracted image to automatically confirm the number of medicines in the package. According to the technique described in Patent Literature 1 (especially, refer to claim 1 of Patent Literature 1), the illumination device includes a scattering surface illumination unit and is provided with a background image forming means that generates a background image distinguishable from the surface illumination unit in the imaging data captured with no object in the imaging range, so as to define the medicine image region based on a perspective image of the background image forming means that appears in the heat sealing portion of the package. That is, by imaging the package from the front side while illuminating the package of the light-scattering sachet sheet from the back side, it is possible to obtain a negative image excluding the influence of the color, the engraving, or the like on the tablet inside the package. Here, the portion (non-sealed portion) of the sachet sheet other than the heat-sealed portion is in the form of ground glass, whereas the heat-sealed portion has lost its light scattering properties and looks like transparent glass. Based on such a difference in scattering properties between the heat-sealed portion and the non-sealed portion during light transmission, the background image on the illumination side is highlighted only in the end portion of the package, thereby enabling detecting and specifying the end portion of the package.

The technique described in Patent Literature 2 relates to a medicine inspection system (corresponding to a medicine verification device) that performs an inspection of a medicine for each of sachets (corresponding to packaging bags) of a continuous sachet (corresponding to a continuous packaging bag). According to the technique described in Patent Literature 2 (especially, refer to claim 7 and Paragraphs 0043 and 0044 of Patent Literature 2), a boundary recess such as a cutout line does not clearly appear in a captured image, and therefore, a candidate for the boundary of the sachet (corresponding to the packaging bag) is selected from the captured images. Specifically, a prescribed value of the length of the sachet as an inspection target is acquired, and a boundary candidate assumed as a boundary between the sachet as an inspection target and sachets adjacent to the sachet on the upstream and downstream sides are derived as an upstream and a downstream boundary candidate respectively on the basis of the captured image of the continuous sachet, thereby acquiring position information regarding the upstream boundary candidate and the downstream boundary candidate. Subsequently, for each of the candidates for the combination of the upstream boundary candidate and the downstream boundary candidate, a calculation based on the acquired position information is performed to derive a candidate value for the length of the sachet as an inspection target. Among the candidate values, a value that is close to the prescribed value for the length of the sachet as an inspection target is selected, and then, a combination of the upstream boundary candidate and the downstream boundary candidate that constitute the selected candidate value will be defined as the boundary position located upstream and downstream of the sachet as an inspection target.

The techniques described in Patent Literatures 3 and 4 relate to a medicine checking device (corresponding to a medicine verification device) for inspecting a medicine for each of sachets, in which each of the sachets (corresponding to packaging bags) in a continuous sachet (corresponding to a continuous packaging bag) is sealed at a vertical seal portion extending in the width direction of the continuous sachet and at a horizontal seal portion extending in the longitudinal direction of the continuous sachet, and the continuous sachet has a boundary formed between the vertical seal portions of adjacent sachets. According to the techniques described in Patent Literatures 3 and 4 (particularly, according to claim 32 of Patent Literature 3 and claim 31 of Patent Literature 4), there is provided a boundary position deriving means capable of deriving a boundary position in a continuous sachet, and the boundary position deriving means detects a contour line (vertical edge) extending in the vertical direction in the captured image region of the sachet, selects a vertical edge longer than a predetermined length, recognizes a region in which an interval between the vertical edges falls within a predetermined interval set on the basis of the width of the vertical seal among the plurality of selected vertical edges, as an edge region, and further recognizes the center of the recognized edge region as a boundary position between the vertical seal portions.

SUMMARY OF THE INVENTION

However, none of the techniques described in Patent Literatures 1 to 4 directly detects a boundary recess such as a cutout line. In particular, the technique described in Patent Literature 1 uses a characteristic having a difference in the scattering property at light transmission between the heat-sealed portion and the non-sealed portion in the sachet sheet so as to highlight the background image on the illumination side only at the package end, thereby detecting and specifying the package end. Accordingly, the technique described in Patent Literature 1 is only applicable to the sachet sheet having a different light scattering properties between the heat-sealed portion and the non-sealed portion, and thus, it would be difficult to apply this technique to a sachet sheet (continuous packaging bag) having no such characteristic.

Moreover, in the technique described in Patent Literature 2, a candidate value of the length of the sachet as an inspection target is derived for each of the candidates for the combination of the upstream boundary candidate and the downstream boundary candidate, and the value that is close to the prescribed value for the length of the sachet as an inspection target is selected out of the derived candidate values, and then a combination of the upstream boundary candidate and the downstream boundary candidate that constitute the selected candidate value will be determined as the boundary position located upstream and downstream of the sachet as an inspection target. That is, a prescribed value of the length of the sachet as an inspection target would be required in order to use the technique described in Patent Literature 2, and therefore, the technique cannot be used when the prescribed value is unknown. In addition, in a case where there are a plurality of upstream boundary candidates or a plurality of downstream boundary candidates, this leads to a case where there are a plurality of candidates having derived values of the length of the sachet as an inspection target close to the prescribed value, among the candidate for combinations of the upstream boundary candidate and the downstream boundary candidate. In such a case, it is difficult to decide the boundary position from among the boundary candidates.

Furthermore, the techniques described in Patent Literatures 3 and 4 recognize an edge region from an interval between vertical edges longer than a predetermined length and then determine the center of the edge region as a boundary position between the vertical seal portions. Accordingly, the techniques described in Patent Literatures 3 and 4 are used under the premise that the package boundary position exists at the center position of the edge region, and thus, it is difficult to accurately specify the position of the boundary recess in a case, for example, where the boundary recess is provided at a position deviated from the center of the edge region.

The present invention has been made in view of the above circumstances and aims to provide a medicine verification device and a boundary recess detection method capable of appropriately detecting the position of a boundary recess provided at a boundary between packaging bags in a continuous packaging bag.

In order to achieve the above object, a medicine verification device of the present invention includes: a detection unit that detects a boundary recess formed at a boundary position between a plurality of packaging bags each of which packs a medicine and is connected to form a continuous packaging bag having a strip-like shape; and an image capturing unit that captures an image of a surface of an imaging target portion on which at least the boundary recess is located a plurality of times while imaging conditions are changed in a state where light is emitted toward the surface of the imaging target portion in the continuous packaging bag, wherein the detection unit detects the boundary recess in the imaging target portion on the basis of the plurality of images captured while changing the imaging conditions by the image capturing unit.

Preferably, the medicine verification device further includes a light irradiation unit that emits light toward the surface of the imaging target portion when the image capturing unit captures an image, wherein the light irradiation unit includes a first light emitting unit and a second light emitting unit that emit light in mutually opposite directions in a longitudinal direction of the continuous packaging bag and emits light diagonally toward the surface of the imaging target portion, the image capturing unit captures an image in a state where the capturing target portion is located between the first light emitting unit and the second light emitting unit in the longitudinal direction, and the light irradiation unit changes a light emitting unit used at the time of light emission out of the first light emitting unit and the second light emitting unit when changing the imaging conditions. Here, "emitting light diagonally toward the surface of the imaging target portion" refers to emission toward the surface of the imaging target portion in a diagonal direction that is a direction inclined with respect to a front direction, when an imaging direction of the imaging target portion is defined as the front direction.

Preferably, the image capturing unit captures a first image of the surface of the imaging target portion while the light irradiation unit emits light toward the surface of the imaging target portion using the first light emitting unit and captures a second image of the surface of the imaging target portion while the light irradiation unit emits light toward the surface of the imaging target portion using the second light emitting unit, and the detection unit detects the boundary recess in the imaging target portion using the first image and the second image.

Preferably, the light emission of the second light emitting unit is stopped during the light emission performed by the light irradiation unit toward the surface of the imaging target portion using the first light emitting unit, and the light emission of the first light emitting unit is stopped during the light emission performed by the light irradiation unit toward the surface of the imaging target portion using the second light emitting unit.

Preferably, the detection unit combines a portion in the first image including an image of a region on a side farther from the first light emitting unit out of the imaging target portion and a portion in the second image including an image of a region on a side farther from the second light emitting unit out of the imaging target portion to create a combined image, and the detection unit detects the boundary recess in the imaging target portion on the basis of the combined image.

Preferably, the image capturing unit includes a first camera and a second camera that images the imaging target portion from mutually opposite directions in a thickness direction of the continuous packaging bag, the first camera captures an image of one surface of the imaging target portion in the thickness direction, the second camera captures an image of another surface of the imaging target portion located on the opposite side to the one surface in the thickness direction, and the detection unit detects the boundary recess in the imaging target portion on the basis of an image captured by the first camera and an image captured by the second camera.

Preferably, the detection unit specifies a candidate for the boundary recess appearing in the image captured by the first camera and specifies a candidate for the boundary recess appearing in the image captured by the second camera, and thereafter, the detection unit detects the candidate for the boundary recess appearing in both the image captured by the first camera and the image captured by the second camera, as the boundary recess in the imaging target portion.

Preferably, a medicine is packaged in the packaging bag of the continuous packaging bag, and the image capturing unit captures an image of a surface of the imaging target portion in which at least an end of the packaging bag in which the medicine is packaged and the boundary recess adjacent to the end are located, a plurality of times the imaging conditions.

Preferably, the packaging bag is light transmissive, the image capturing unit captures an image of a surface of the imaging target portion in which at least a portion covering the medicine, the end, and the boundary recess adjacent to the end are located, out of the packaging bag in which the medicine is packaged, a plurality of times the imaging conditions, and the medicine verification device further comprises a removal process execution unit that performs, on each of the plurality of images captured under different imaging conditions, a removal process for removing an image of a medicine in each of the plurality of images.

Preferably, the removal process execution unit executes the removal process of removing the image of the medicine in the image by removing a post-contraction-dilation image obtained by applying contraction and dilation on a pixel group constituting the image captured by the image capturing unit in at least one direction from an image before application of the contraction and dilation.

Preferably, the boundary recess is a cutout line formed by a dashed linear groove formed from one end to the other end of the continuous packaging bag in a lateral width direction of the continuous packaging bag.

In order to achieve the above object, a boundary recess detection method of the present invention is a method of detecting a boundary recess formed at a boundary position between a plurality of packaging bags each of which packs a medicine and is connected to form a continuous packaging bag having a strip-like shape, and the method includes: a step of capturing an image of a surface of an imaging target portion on which at least the boundary recess is located a plurality of times while imaging conditions are changed in a state where light is emitted toward the surface of the imaging target portion in the continuous packaging bag; and a step of detecting the boundary recess in the imaging target portion on the basis of the plurality of images captured the imaging conditions.

With the medicine verification device and the boundary recess detection method according to the present invention, it is possible to appropriately detect the position of the boundary recess provided in the boundary between packaging bags in a continuous packaging bag. As a result, when verifying the suitability of the medicine packed in the packaging bag, it is possible to properly perform the verification with accurately defined imaging range of the continuous packaging bag.

DETAILED DESCRIPTION OF THE INVENTION

Hereinafter, a medicine verification device and a medicine verification method of the present invention will be described in detail.

Although the description of the components described below might be made based on typical embodiments of the present invention, the present invention is not limited to such embodiments. That is, the following embodiments are an example provided to facilitate understanding of the medicine verification device and the medicine verification method of the present invention and would not limit the present invention. Accordingly, various improvements or changes may be made without departing from the scope and spirit of the present invention.

In addition, in the present description, a "medicine" represents a solid medicine, and specifically corresponds to a tablet or a capsule.

«Medicine Prescription Operation»

Figure 1:
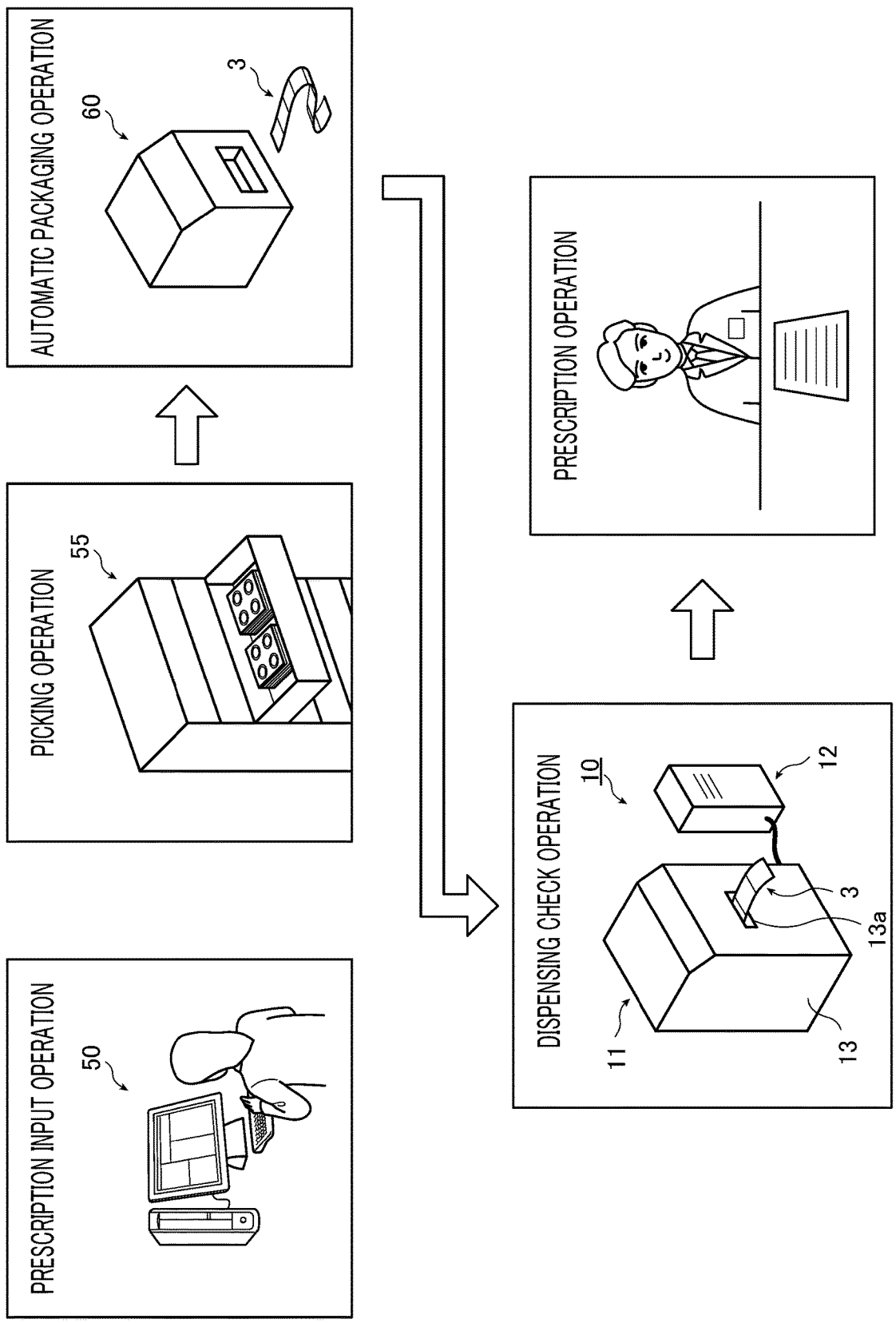
FIG. 1 is a view illustrating a flow of a medicine prescription operation.

Before describing the medicine verification device (hereinafter, a medicine verification device 10) according to one embodiment of the present invention, a medicine prescription operation performed using the medicine verification device 10 will be outlined first. The medicine prescription operation includes operations sequentially performed in the order of a prescription input operation, a picking operation, an automatic packaging operation, a dispensing inspection operation, and a prescription operation, as illustrated in FIG. 1. FIG. 1 is a view illustrating a flow of the medicine prescription operation.

In the prescription input operation, a pharmacist inputs prescription conditions described in a prescription to a computer (hereinafter, prescription condition input device 50). Here, a prescription condition is a condition set for prescribing a medicine to a patient. Examples of input prescription conditions include the name and age of the patient, the type of medicine to be prescribed, the prescription quantity for each of types. The following description assumes that medicines are taken by a plurality of doses and that the prescription quantity for one dose is the same. However, the prescription condition is not limited to this, and a medicine for only one dose may be prescribed. Furthermore, the type and the prescription quantity of the medicine for one dose may be different each of times.

In the picking operation, on the basis of prescription conditions, a pharmacist picks medicines of the types corresponding to the prescription conditions from a medicine shelf 55 by the quantities according to the prescription conditions. Note that the picking operation is not limited to the case where the pharmacist performs the operation manually, but may be performed automatically by a known automatic picking device on the basis of the prescription conditions input to the prescription condition input device 50.

Furthermore, each of the medicines picked in the present embodiment includes identification information formed on a medicine surface. The "identification information" includes characters, numerals, symbols, or the like for identifying the type of medicine (medicine type) and is formed by engraving or printing. In the present embodiment, it is assumed that identification information is formed on the surface of the medicine by engraving (recess processing). However, the medicine to be picked is not limited to the above-described embodiment, and medicines to be picked may include medicines for which identification information is not formed or may include medicines for which identification information is formed by printing.

In the automatic packaging operation, the pharmacist sets the medicines picked in the picking operation onto a tray of a packaging machine 60 illustrated in FIG. 1, and then, the packaging machine 60 automatically packages the medicines in the tray. At this time, the picked medicines are set on a tray for one dose, and the medicines for one dose are packaged in each of the plurality of packaging bags 1. The packaging bag 1 is a known light-transmissive sachet. Examples of the material of the packaging bag 1 include a laminated film of cellophane and polyethylene, and a polyethylene film.

Figure 2:
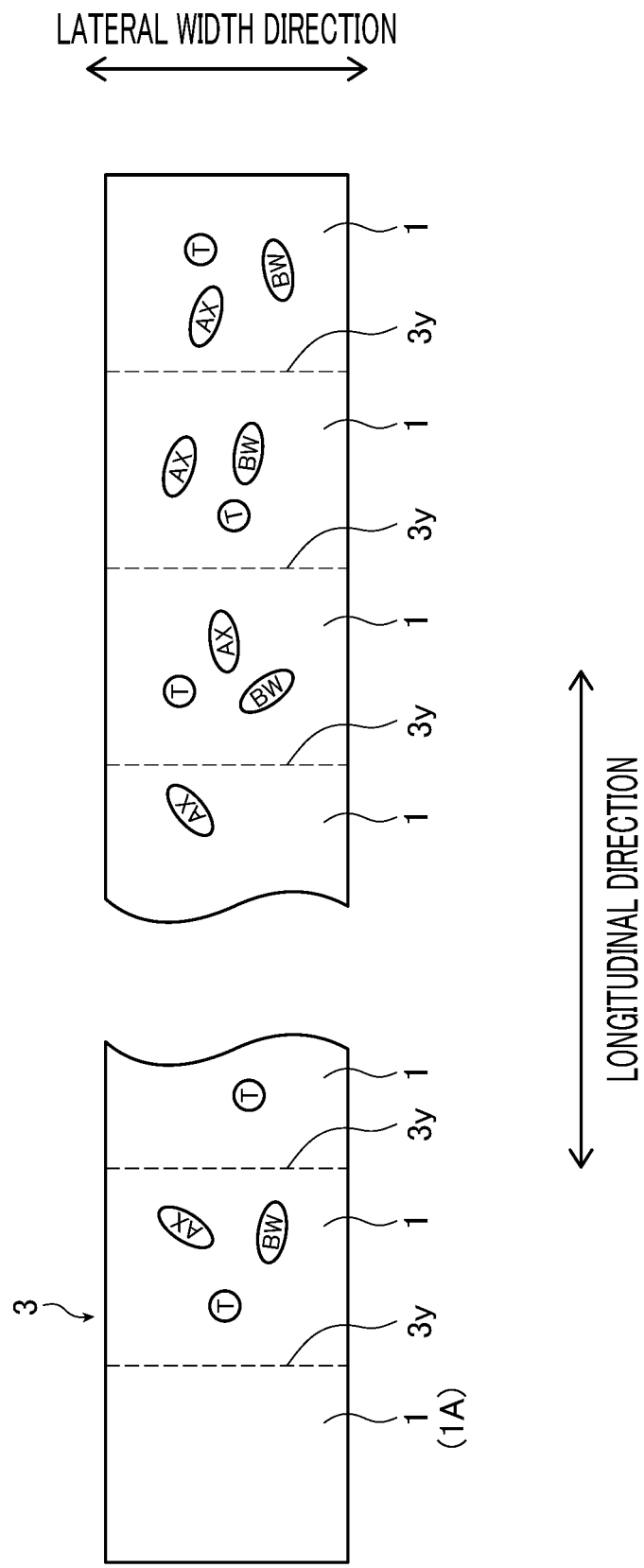
FIG. 2 is a view illustrating a continuous packaging bag.

At a point of completion of the automatic packaging operation, the plurality of packaging bags 1 each containing the medicines are continuously arranged to form a continuous packaging bag 3 having a strip-like shape as illustrated in FIG. 2. At the time of taking the medicine, a patient separates one packaging bag 1 from the continuous packaging bag 3 and takes the medicine packed in the separated packaging bag 1. FIG. 2 is a view illustrating the continuous packaging bag 3.

The continuous packaging bag 3 will be described. Picked medicines are packaged in the packaging bag 1 (excluding an empty bag 1A described below) of the continuous packaging bag 3. Furthermore, as observed from FIG. 2, a cutout line $3y$ as a boundary recess is formed at a boundary position between the packaging bags 1 in the continuous packaging bag 3. Here, the cutout line $3y$ is formed by a broken line-shaped linear groove, and is formed from one end to the other end of the continuous packaging bag 3 in the lateral width direction of the continuous packaging bag 3. In addition to the cutout line $3y$, a cutout having a triangular shape, a rectangular shape, a semi-elliptical shape, or the like may be formed at an end portion in the lateral width direction of the continuous packaging bag 3, as the boundary recess.

At a point of completion of the automatic packaging operation, the packaging bag 1 located at one end of the continuous packaging bag 3 is an empty bag 1A as illustrated in FIG. 2. The empty bag 1A is similar to the packaging bag 1 packing the medicine, except for not containing the medicine inside. The empty bag 1A may be provided at a location other than the end of the continuous packaging bag 3. Moreover, there is no need to include the empty bag 1A in the continuous packaging bag 3.

In the dispensing inspection operation, inspection of whether the prescribed medicine is correct is performed using the medicine verification device 10 illustrated in FIG. 1. Specifically, the medicine verification device 10 verifies whether the type and number (more precisely, the number of each of types) of the medicines packed in each of the packaging bags 1 in the continuous packaging bag 3 is as instructed in the prescription.

The prescription operation performs prescription of prepackaged medicines determined to be correct (as instructed by the prescription) in the dispensing inspection operation, for the patient (prescription destination). At this time, the pharmacist removes the empty bag 1A located at one end of the continuous packaging bag 3 and hands the remaining continuous packaging bag 3 to the patient.

«Configuration of Medicine Verification Device»

Next, a configuration of the medicine verification device 10 will be described.

The medicine verification device 10 is used for dispensing inspection and verifies whether the type and the number (more precisely, the number of each of types) of the medicines packed in the packaging bag 1 packed in the automatic packaging operation are the proper types and number. Here, the proper type and the number are the type of the medicine and the number of each of types on which an instruction is given in the prescription (in other words, input as prescription conditions), which are more precisely the type and number of the medicine for one dose.

Note that the medicine packed (packaged) in each of the packaging bags 1 excluding the empty bag 1A in the continuous packaging bag 3 corresponds to the verification target medicine.

As illustrated in FIG. 1, the medicine verification device 10 includes: a device main body 11 having a function of capturing an image of a medicine as a verification target (specifically, a medicine packed in each of the packaging bags 1); and a processing device 12 having a function of performing dispensing inspection based on the image captured by the device main body 11.

Figure 3:
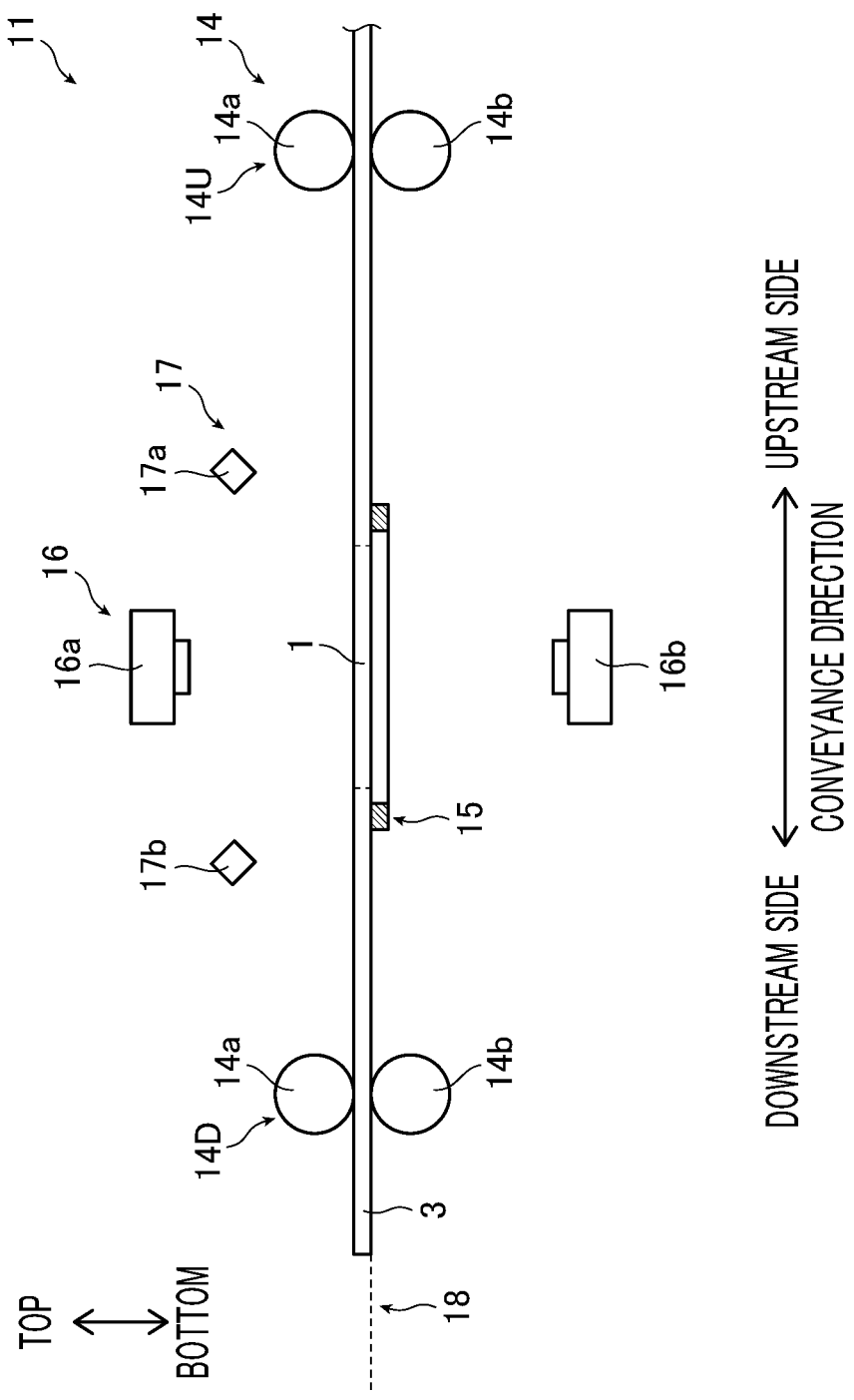
FIG. 3 is a schematic view illustrating an internal structure of a device main body included in the medicine verification device according to one embodiment of the present invention.

The device main body 11 includes a housing 13 illustrated in FIG. 1, and includes, within the housing 13, a conveyance unit 14, an arrangement unit 15, an image capturing unit 16, and a light irradiation unit 17 illustrated in FIG. 3. FIG. 3 is a schematic view illustrating an internal structure of the device main body 11. In addition, the housing 13 of the device main body 11 includes: an introduction part 13a for introducing the continuous packaging bag 3 to the inside of the device main body 11; and a discharge part (not illustrated) for discharging the continuous packaging bag 3 introduced inside the device main body 11 to the outside of the device main body 11.

The conveyance unit 14 includes a conveyance path 18 formed inside the device main body 11 and conveys the continuous packaging bag 3 along the conveyance path 18. The continuous packaging bag 3 introduced into the inside of the device main body 11 from the introduction part 13a moves toward the downstream side of the conveyance path 18 by the conveyance operation of the conveyance unit 14 and eventually passes through the discharge part to be discharged to the outside of the device main body 11. Here, the "downstream side" means a side closer to the discharge part in the conveyance direction, and an "upstream side" means a side opposite to the downstream side, that is, a side closer to the introduction part 13a in the conveyance direction.

In the present embodiment, the conveyance path 18 is a horizontal path, and the conveyance unit 14 performs conveyance in a state where a longitudinal direction of the continuous packaging bag 3 runs along the conveyance path 18 (that is, the conveyance direction) and where a thickness direction of the continuous packaging bag 3 runs along the up-down direction (vertical direction).

As illustrated in FIG. 3, the conveyance unit 14 includes an upstream drive unit 14U and a downstream drive unit 14D. The upstream drive unit 14U is arranged on the upstream side of the arrangement unit 15, while the downstream drive unit 14D is arranged on the downstream side of the arrangement unit 15. Each of the upstream drive unit 14U and the downstream drive unit 14D includes a pair of upper and lower nip rollers 14a and 14b, and a motor (not illustrated) that rotationally drives one of the pair of upper and lower nip rollers 14a and 14b. The pair of upper and lower nip rollers 14a and 14b is arranged with a gap enough to allow the continuous packaging bag 3 to pass through, and the rollers rotate in a state of nipping the continuous packaging bag 3 between the rollers. With this configuration, the continuous packaging bag 3 is conveyed in a state where a slight tension is applied.

In the present embodiment, the motor is configured to rotate intermittently. Therefore, the conveyance unit 14 performs the conveyance operation intermittently. In one conveyance operation, the continuous packaging bag 3 moves by a predetermined amount in the conveyance direction. The movement amount (conveyance amount) of the continuous packaging bag 3 in one conveyance operation is set by the control unit 21 of the processing device 12 described below.

Note that the conveyance unit 14 of the present embodiment can perform conveyance to either the upstream side or the downstream side in the conveyance direction by switching the rotational direction of the motor. The conveyance direction is set by the control unit 21 of the processing device 12.

Furthermore, while the present embodiment is an example that applies the conveyance mechanism using the rotation drive of the roller (that is, a roller conveyor), it is also allowable to use other conveyance mechanisms as long as the mechanism can convey the continuous packaging bag 3 properly. For example, it is allowable to apply a belt conveyor that conveys the continuous packaging bag 3 by rotating an endless belt while the continuous packaging bag 3 is mounted on the upper surface of the belt.

The arrangement unit 15 is a portion where the verification target medicine is disposed in a state of being packed in the packaging bag 1 and is provided at an intermediate position of the conveyance path 18 as illustrated in FIG. 3. The arrangement unit 15 is a rectangular frame-shaped base and has a size on which one packaging bag 1 can be mounted. In addition, the packaging bags 1 disposed on the arrangement unit 15 in the continuous packaging bag 3 are sequentially switched together with the conveyance of the continuous packaging bag 3 by the conveyance unit 14.

Note that, in a state where the packaging bag 1 is disposed on the arrangement unit 15, the entire region of the upper surface of the packaging bag 1 (the surface facing the upper side of the device main body 11, the similar applies hereinafter) is exposed, while regions other than the edge of the lower surface of the packaging bag 1 (the surface facing the lower side of the device main body 11, the similar applies hereinafter) are exposed. The edge of the packaging bag 1 is a sealed portion formed by stacking and pressing two film sheets constituting the packaging bag 1 together.

The image capturing unit 16 captures an image of the packaging bag 1 disposed on the arrangement unit 15 and an image of the medicine (that is, the verification target medicine) packed in the packaging bag 1. As illustrated in FIG. 3, the image capturing unit 16 includes two cameras, upper and lower, as a plurality of cameras. The two cameras image the portion disposed on the arrangement unit 15 in the continuous packaging bag 3 (that is, an imaging target portion 3x) from mutually opposite directions in the thickness direction (that is, up-down direction) of the continuous packaging bag 3.

Specifically, the camera on the upper side (hereinafter, referred to as a first camera 16a) out of the upper and lower two cameras is disposed immediately above the arrangement unit 15 and captures an image of one surface of the imaging target portion 3x in the thickness direction of the continuous packaging bag 3, more specifically, an image of an upper surface of the packaging bag 1 disposed on the arrangement unit 15, from above. The camera on the lower side (hereinafter, referred to as a second camera 16b) is disposed immediately below the arrangement unit 15 and captures an image of another surface of the imaging target portion 3x located on opposite side of the one surface (that is, the surface captured by the first camera 16a) in the thickness direction of the continuous packaging bag 3, more specifically, an image of a lower surface of the packaging bag 1 disposed on the arrangement unit 15, from below.

The images of the packaging bag 1 (excluding the empty bag 1A) captured by the first camera 16a and the second camera 16b include an image of medicines. Here, the "medicine image" or "image of a medicine" means an image of the medicines captured through the packaging bag 1.

The device main body 11 in the present embodiment has a configuration in which the conveyance operation by the conveyance unit 14 is performed intermittently, and the image capturing unit 16 captures an image of the packaging bag 1 disposed on the arrangement unit 15 and an image of a medicine packed in the packaging bag 1 between the conveyance operations. In addition, every time the packaging bag 1 disposed on the arrangement unit 15 is switched by the conveyance operation, the image capturing unit 16 captures the image of the packaging bag 1 disposed on the arrangement unit 15 and the image of the medicine packed in the packaging bag 1.

Figure 4:
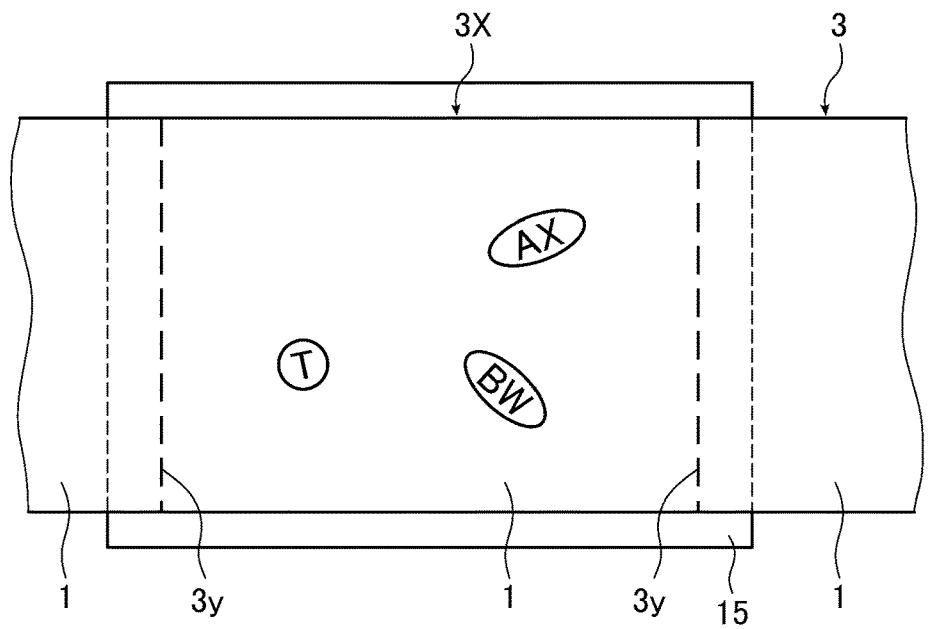
FIG. 4 is a view illustrating an imaging range of an image capturing unit and a part of a continuous packaging bag included in the range.

In the present embodiment, the imaging range (angle of view) of the first camera 16a is set to a rectangular region as illustrated in FIG. 4 (a rectangular region illustrated by a broken line in FIG. 4), which is a range capable of imaging an entire surface of the upper surface of the packaging bag 1 disposed on the arrangement unit 15 and a part (more precisely, an end portion) of the upper surface of the packaging bag 1 located on both sides of the packaging bag 1 disposed on the arrangement unit 15. In other words, the portion of the continuous packaging bag 3 that is within the imaging range of the first camera 16a corresponds to the imaging target portion 3x, and at least the cutout line 3y between the packaging bags 3 is located at this portion as illustrated in FIG. 4.

FIG. 4 is a view illustrating an imaging range of the image capturing unit 16 and a part of the continuous packaging bag 3 included in the range.

Similarly, the imaging range (angle of view) of the lower camera 16b is set to a rectangular region, which is a range capable of imaging a region on the lower surface of the packaging bag 1 disposed on the arrangement unit 15 that is inside the arrangement unit 15 and is exposed, and a portion (more precisely, an end portion) of the lower surface of the packaging bag 1 located on both sides of the packaging bag 1 disposed on the arrangement unit 15. In other words, the portion of the continuous packaging bag 3 that is within the imaging range of the second camera 16b corresponds to the imaging target portion 3x, and at least the cutout line 3y between the packaging bags 1 is located at this portion.

The image capturing unit 16 may be any type as long as it has a function of acquiring image data of a subject. Examples of this include a Charge-Coupled Device (CCD) image sensor and a Complementary Metal Oxide Semiconductor (CMOS) image sensor, although the present invention is not limited to these.

Furthermore, the image capturing unit 16 in the present embodiment is implemented by two cameras, but the number of cameras is not particularly limited and may be one, or three or more.

Furthermore, in the present embodiment, the camera is installed at a position vertically sandwiching the arrangement unit 15. However, the installation position of the camera can be set to any position as long as the packaging bag 1 disposed on the arrangement unit 15 and the medicine packed in the packaging bag 1 can be imaged satisfactorily.

The light irradiation unit 17 is configured to perform light emission to the packaging bag 1 disposed on the arrangement unit 15 and the medicine packed in the packaging bag 1 (that is, the verification target medicine) when the image capturing unit 16 captures an image. More specifically, the light irradiation unit 17 performs light emission toward a portion (that is, the surface of the imaging target portion 3x) within the imaging range of the image capturing unit 16 out of the continuous packaging bag 3.

Figure 5:
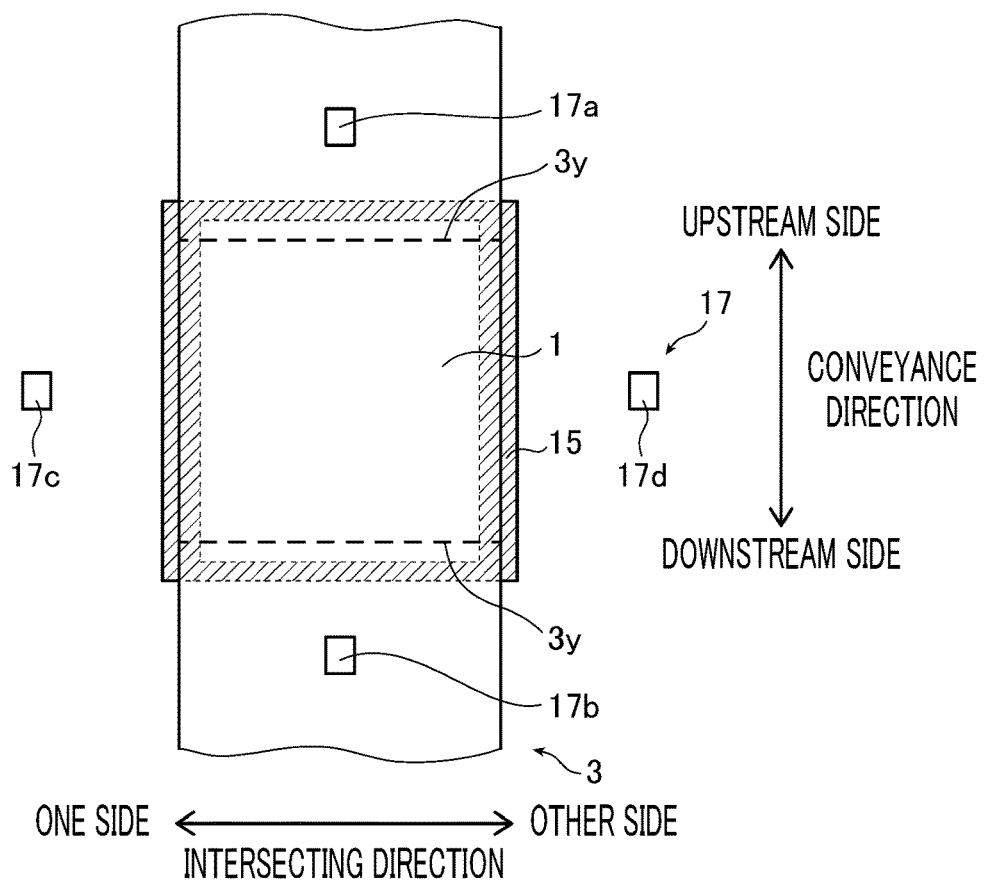
FIG. 5 is a schematic top view of a plurality of light emitting units of the light irradiation unit.

As illustrated in FIG. 5, the light irradiation unit 17 has a plurality of light emitting units, specifically four light emitting units 17a, 17b, 17c, and 17d in the present embodiment. FIG. 5 is a schematic top view of a plurality of light emitting units of the light irradiation unit 17. The four light emitting units 17a, 17b, 17c, and 17d are light sources used when the light irradiation unit 17 performs light emission, and individually arranged on four sides of the arrangement unit 15 as illustrated in FIG. 5. The light irradiation unit 17 performs light emission in different directions using the four light emitting units 17a, 17b, 17c, and 17d (a plurality of light emitting units).

More specifically, the two light emitting units 17a and 17b are arranged at positions opposite to each other as viewed from the arrangement unit 15 in the conveyance direction (that is, the longitudinal direction of the continuous packaging bag 3), and the two units emit light in mutually opposite directions. That is, one light emitting unit 17a (hereinafter, referred to as a first light emitting unit 17a) emits light from the upstream side in the conveyance direction to the arrangement unit 15 located downstream in the conveyance direction. The other light emitting unit 17b (hereinafter, referred to as a second light emitting unit 17b) emits light from the downstream side in the conveyance direction to the arrangement unit 15 located upstream in the conveyance direction.

The remaining two light emitting units 17c and 17d out of the four light emitting units 17a, 17b, 17c, and 17d are arranged at positions opposite to each other as viewed from the arrangement unit 15 in a direction (hereinafter, intersecting direction) intersecting the conveyance direction, and the units emit light in mutually opposite directions. That is, one light emitting unit 17c (hereinafter, referred to as a third light emitting unit 17c) emits light from one side in the intersecting direction toward the arrangement unit 15 on the other side. The other light emitting unit 17d (hereinafter, referred to as a fourth light emitting unit 17d) emits light to the arrangement unit 15 on one side, from the other side, in the intersecting direction. Here, "one side in the intersecting direction" means, for example, a side near one end of the arrangement unit 15 in the intersecting direction, while "the other side in the intersecting direction" means a side close to the other end of the arrangement unit 15 in the intersecting direction.

The light irradiation unit 17 uses a part or all of the four light emitting units 17a, 17b, 17c, and 17d to perform light emission to the packaging bag 1 disposed on the arrangement unit 15 and the medicine packed in the packaging bag 1. At this time, as observed from FIG. 6, the light irradiation unit 17 performs light emission diagonally toward the surface of the imaging target portion 3x. This direction is advantageous because applying light diagonally to the surface of the medicine can emphasize the contour of the identification information formed on the surface of the medicine (in particular, an edge portion of the contour at the object of light emission).

Figure 6:
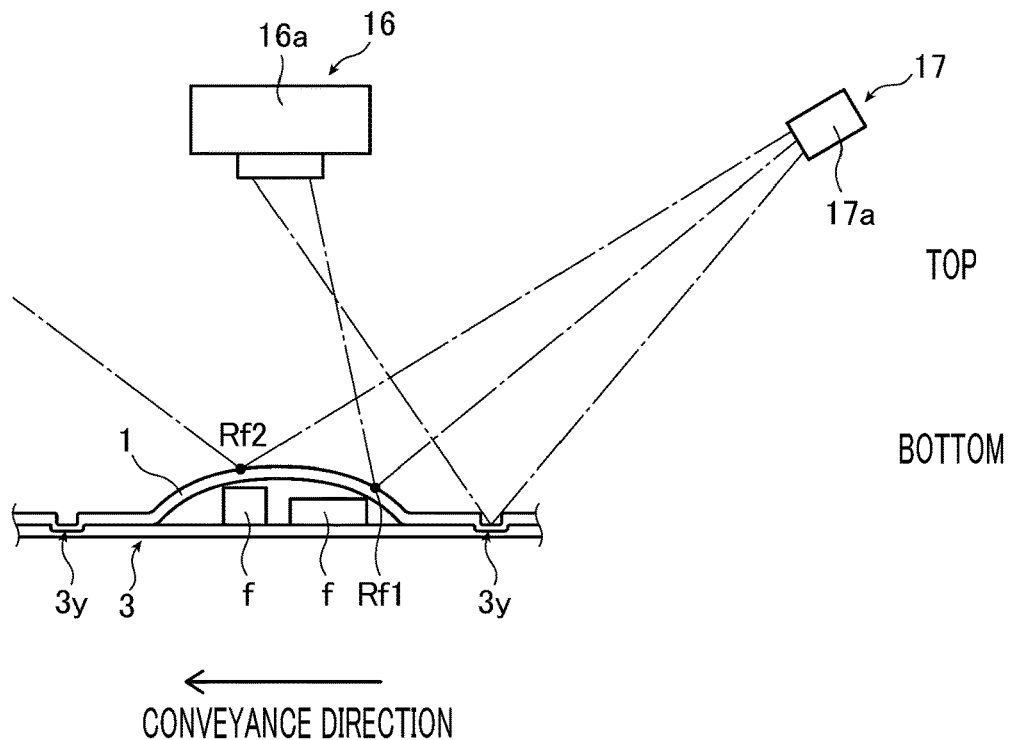
FIG. 6 is a schematic view illustrating a state where light is applied to a packaging bag.

FIG. 6 is a view illustrating a state in which the packaging bag 1 is irradiated with light, which is also a schematic side view illustrating the packaging bag 1, the image capturing unit 16, and the light irradiation unit 17.

In addition, in the present embodiment, it is possible to switch the light emitting units 17a, 17b, 17c, and 17d used by the light irradiation unit 17 when the image capturing unit 16 captures an image. Specifically, the light irradiation unit 17 performs light emission using one of the four light emitting units 17a, 17b, 17c, and 17d. At this time, the other light emitting units are stopped with no light emission. For example, while the light irradiation unit 17 emits light toward the surface of the imaging target portion 3x using the first light emitting unit 17a, each of the units, namely, the second light emitting unit 17b, the third light emitting unit 17c and the fourth light emitting unit 17d, stops light emission. Similarly, while the light irradiation unit 17 emits light toward the surface of the imaging target portion 3x using the second light emitting unit 17b, each of the units, namely, the first light emitting unit 17a, the third light emitting unit 17c and the fourth light emitting unit 17d, stops light emission.

While the light irradiation unit 17 performs light emission from one light emitting unit, the image capturing unit 16 captures an image of the medicine packed in the packaging bag 1 disposed on the arrangement unit 15, by one imaging. Thereafter, the light irradiation unit 17 switches one light emitting unit used immediately before to another light emitting unit among the light emitting units 17a, 17b, 17c, and 17d and then, performs light emission using the light emitting unit 17a, 17b, 17c, or 17d after the switching. In the meantime, the image capturing unit 16 captures an image of the medicine packed in the packaging bag 1 disposed on the arrangement unit 15 again.

Thereafter, the light irradiation unit 17 sequentially switches the light emitting units 17a, 17b, 17c, and 17d using the similar procedure, and the image capturing unit 16 captures an image of the medicine packed in the packaging bag 1 disposed on the arrangement unit 15 every time the light irradiation unit 17 switches the light emitting units 17a, 17b, 17c, and 17d. This results in acquisition of captured images for each of the light irradiation directions (that is, four images having mutually different reflection states of light at each of portions of the medicine surface) for the medicine packed in one packaging bag 1 disposed on the arrangement unit 15.

As described above, in the present embodiment, the image capturing unit 16 captures an image of the surface of the imaging target portion 3x under various imaging conditions a plurality of times in a state where the unit performs light emission toward the surface of the imaging target portion 3x in the continuous packaging bag 3. Here, the imaging conditions correspond to the camera used by the image capturing unit 16 at the time of imaging, the light emitting unit used by the light irradiation unit 17 at the time of light emission, or the like.

More specifically, at the time of changing imaging conditions, the light irradiation unit 17 changes the light emitting unit used in light emission among the first light emitting unit 17a, the second light emitting unit 17b, the third light emitting unit 17c, and the fourth light emitting unit 17d. Furthermore, when changing the imaging conditions, the image capturing unit 16 changes the camera used for capturing an image among the first camera 16a and the second camera 16b. Eventually, as a result of the imaging in which the image capturing unit 16 captures images of the imaging target portion 3x the imaging conditions (for each of the imaging conditions), a total of eight shots (the number of cameras×the number of light emitting units) will be imaged for each of the packaging bags 1 in the continuous packaging bag 3.

Moreover, in the present embodiment, as illustrated in FIG. 5, the first light emitting unit 17a is located upstream of the arrangement unit 15 and the second light emitting unit 17b is located downstream of the arrangement unit 15 in the conveyance direction (in other words, the longitudinal direction of the continuous packaging bag 3). Furthermore, the first camera 16a is disposed immediately above the arrangement unit 15, and the second camera 16b is disposed immediately below the arrangement unit 15. With such a positional relationship, the image capturing unit 16 is to capture an image of the surface of the imaging target portion 3x while the imaging target portion 3x is located between the first light emitting unit 17a and the second light emitting unit 17b in the conveyance direction.

Here, as described above, an end of the packaging bag 1 disposed on the arrangement unit 15 (more precisely, the packaging bag 1 in which the medicine is packaged, other than the empty bag 1A), and the cutout line 3y adjacent to the end are located in the imaging target portion 3x. More specifically, the imaging target portion 3x is a portion of the packaging bag 1 disposed on the arrangement unit 15 in which a portion covering the medicine, both ends in the conveyance direction, and the cutout line 3y adjacent to each of the ends are at least located. The image capturing unit 16 captures an image of the surface of the imaging target portion 3x a plurality of times imaging conditions.

Figure 7A:
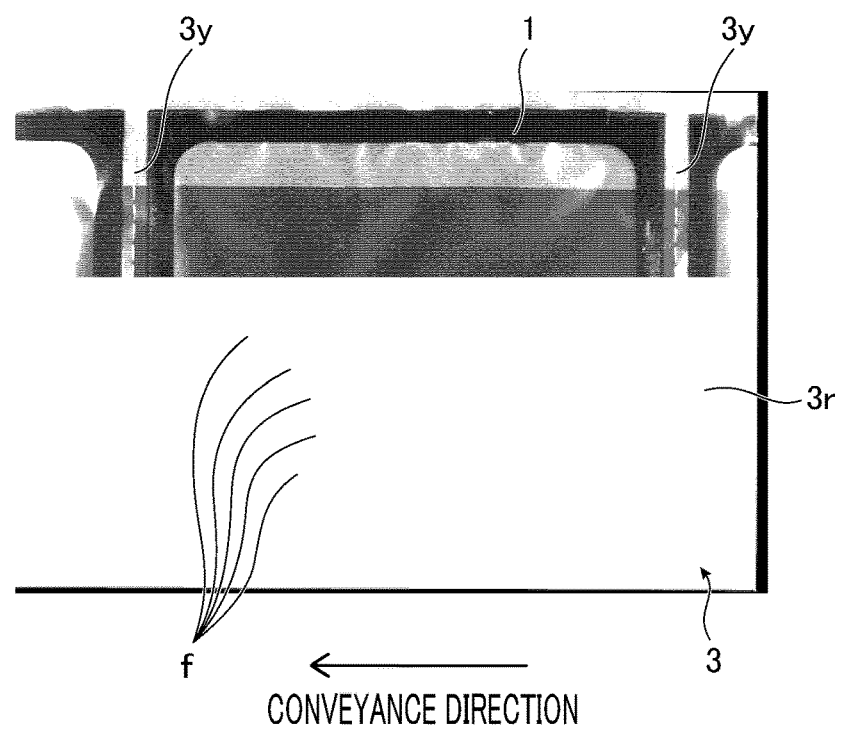
FIG. 7A is an example (part 1) of an image captured by an image capturing unit included in a medicine verification device according to one embodiment of the present invention.
Figure 7B:
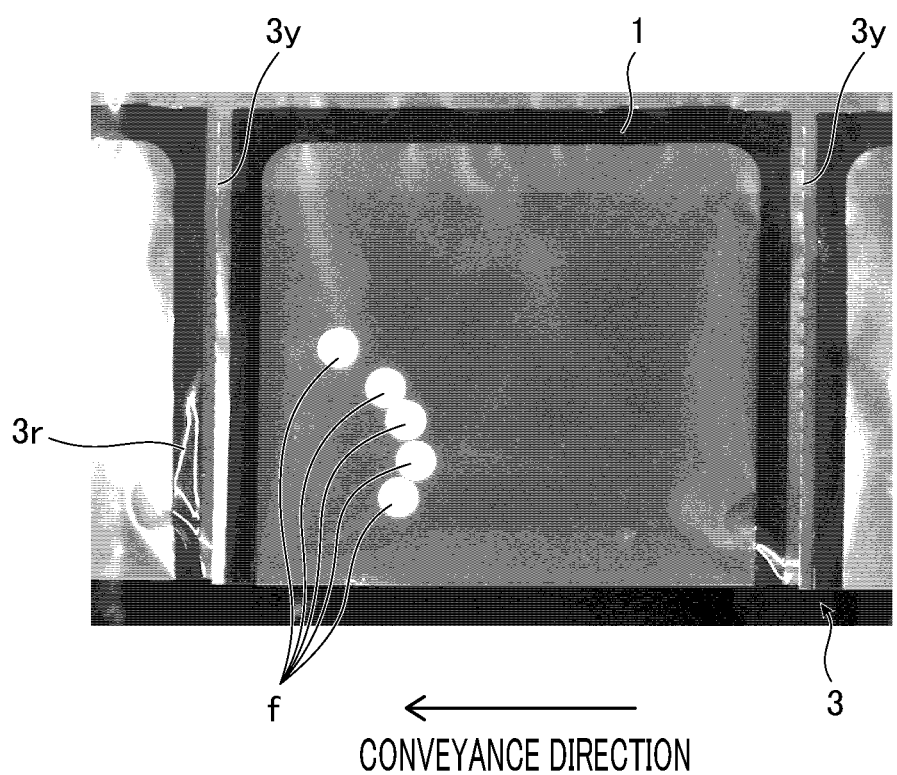
FIG. 7B is an example (part 2) of an image captured by an image capturing unit included in a medicine verification device according to one embodiment of the present invention.

Here, the image of the surface of the imaging target portion 3x captured by the image capturing unit 16 will be described. As illustrated in FIGS. 7A and 7B, the image includes images of the packaging bag 1 disposed on the arrangement unit 15, the cutout lines 3y located on both sides of the packaging bag 1, and each of medicines f packed in the packaging bag 1. FIGS. 7A and 7B are an example of images captured by the image capturing unit 16.

The image illustrated in FIG. 7A and the image illustrated in FIG. 7B are images captured under different imaging conditions. The image illustrated in FIG. 7A is an image of the surface of the imaging target portion 3x captured by the image capturing unit 16 while the light irradiation unit 17 performs light emission toward the surface of the imaging target portion 3x using the first light emitting unit 17a. This image is hereinafter referred to as a "first image". In contrast, the image illustrated in FIG. 7B is an image of the surface of the imaging target portion 3x captured by the image capturing unit 16 while the light irradiation unit 17 performs light emission toward the surface of the imaging target portion 3x using the second light emitting unit 17b. This image is hereinafter referred to as a "second image".

Incidentally, the light emitting units 17a, 17b, 17c, and 17d used by the light irradiation unit 17 for light emission may be implemented with known light sources, including any of a point light source, a line light source, or a surface light source. Specifically, examples of applicable light sources include: electroluminescence types such as Light Emitting Diode (LED), semiconductor laser (Laser Diode (LD)), and organic Electro-luminescence (EL), radiant heat types such as halogen bulbs and incandescent bulbs, discharge emission types such as a mercury lamp and a fluorescent lamp, and a combination of these light sources with a light guide member such as a light guide plate or an optical fiber.

Furthermore, the present embodiment uses the light irradiation unit 17 having four light emitting units 17a, 17b, 17c, and 17d. However, the number of light emitting units is not particularly limited, and it is sufficient as long as two or more light emitting units are provided.

The processing device 12 executes a series of information processing in the implementation of the dispensing inspection. In the present embodiment, the processing device 12 is constituted using a personal computer (PC) external to the device main body 11. However, the present invention is not limited to this, and the processing device 12 may be constituted using a computer built in the device main body 11.

Furthermore, the processing device 12 is communicably connected to the device main body 11, the prescription condition input device 50, and a database server 70 described below. The connection method between the processing device 12 and each device may be a wired connection method or a wireless connection method.

Figure 8:
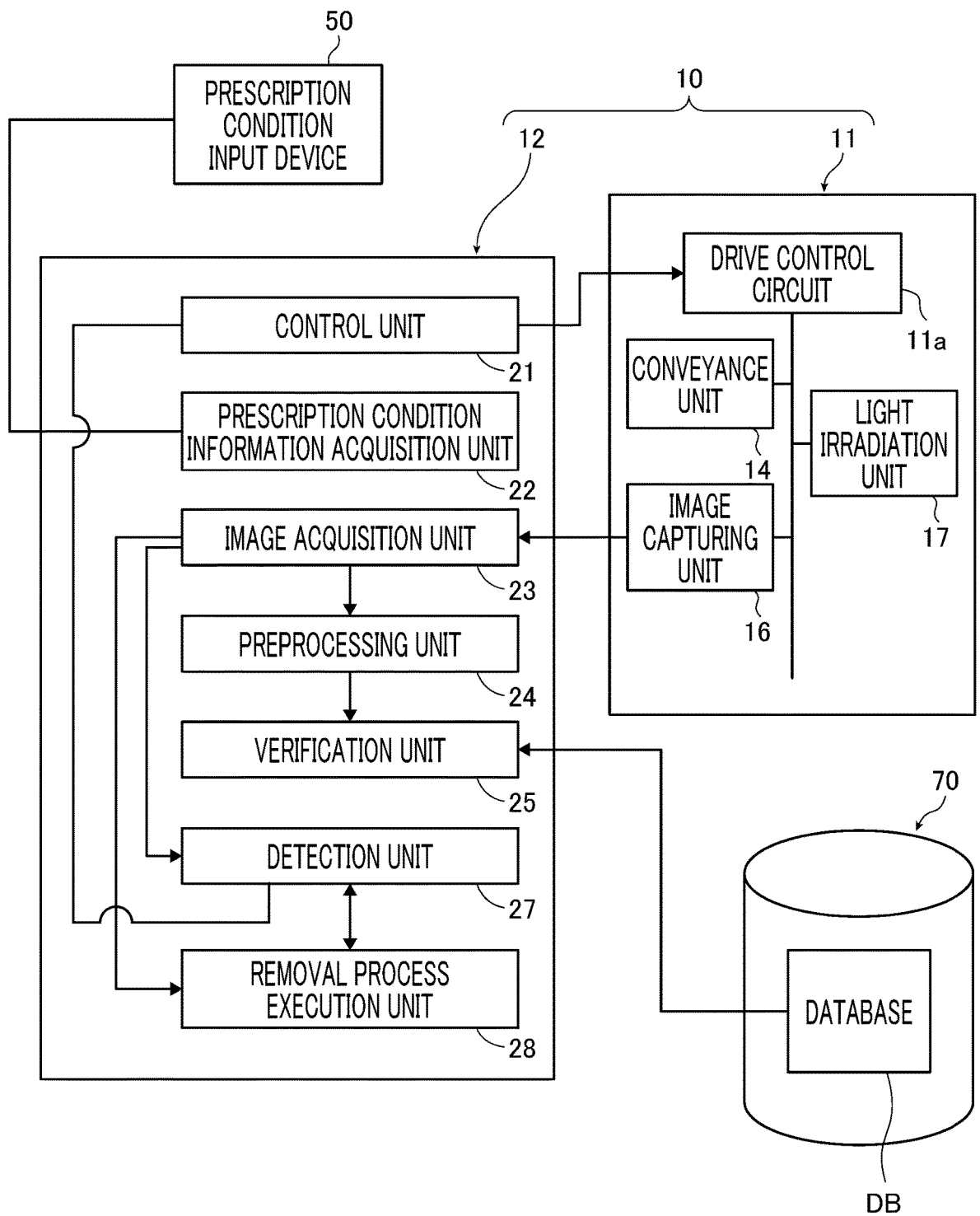
FIG. 8 is a block diagram illustrating a configuration of a processing device included in a medicine verification device according to one embodiment of the present invention.

Furthermore, as illustrated in FIG. 8, the processing device 12 includes a control unit 21, a prescription condition information acquisition unit 22, an image acquisition unit 23, a preprocessing unit 24, a verification unit 25, a detection unit 27, and a removal process execution unit 28. FIG. 8 is a block diagram illustrating a configuration of the processing device 12. These units are implemented by cooperation of hardware devices such as a Central Processing Unit (CPU) and a memory (not illustrated) included in the processing device 12, and an information processing program stored in the processing device 12. The information processing program may be read and obtained from a recording medium such as a Compact Disc Read Only Memory (CD-ROM) storing the program, or may be downloaded and obtained from a predetermined site via a network.

In the present embodiment, individual functional units of the processing device 12 (specifically, the control unit 21, the prescription condition information acquisition unit 22, the image acquisition unit 23, the preprocessing unit 24, the verification unit 25, the detection unit 27, and the removal process execution unit 28) are constituted by one personal computer. However, the present invention is not limited to this, and it is allowable to use a configuration in which a part of the above functional units is constituted by one personal computer while the remaining functional units are constituted by another personal computer.

The control unit 21 is electrically connected to each of units of the device main body 11 (specifically, the conveyance unit 14, the image capturing unit 16, and the light irradiation unit 17) via a drive control circuit 11a mounted on the device main body 11 and controls each of the units of the device. More specifically, the control unit 21 performs control related to the conveyance operation of the conveyance unit 14, such as controlling a conveyance amount, a conveyance direction, a conveyance operation timing, or the like in one conveyance operation. In addition, the control unit 21 performs control related to the imaging operation of the image capturing unit 16, such as controlling a camera to be used among the two cameras 16a and 16b of the image capturing unit 16, and a timing of imaging. In addition, the control unit 21 performs control related to the light emitting operation of the light irradiation unit 17, such as controlling the light emitting unit to use among the four light emitting units 17a, 17b, 17c, and 17d included in the light irradiation unit 17, and the timing of light emission.

The prescription condition information acquisition unit 22 is communicably connected to the prescription condition input device 50 and acquires prescription condition information by communicating with the prescription condition input device 50. Here, the prescription condition information is information indicating the prescription condition, which specifically is electronic data indicating the prescription condition input to the prescription condition input device 50 by the pharmacist.

In the present embodiment, when the input of the prescription condition is completed in the prescription condition input device 50, the prescription condition information is automatically transmitted from the prescription condition input device 50 to the prescription condition information acquisition unit 22, and then the prescription condition information acquisition unit 22 receives the above prescription condition information. However, the present invention is not limited to this. It is also allowable to use a configuration in which an information transmission request is transmitted from the prescription condition information acquisition unit 22, and the prescription condition input device 50 transmits the prescription condition information at a point of reception of the request by the prescription condition input device 50. More specifically, character string information or the two-dimensional barcode information for specifying the prescription condition is printed on a tip portion of the continuous packaging bag 3 (a portion of the continuous packaging bag 3 first introduced into the device main body 11). The prescription condition information acquisition unit 22 reads the above-described printed information when the continuous packaging bag 3 is introduced into the device main body 11. Thereafter, based on the read printed information, the prescription condition information acquisition unit 22 requests a prescription condition information indicating prescription conditions related to the medicine packaged in each of the packaging bags 1 of the continuous packaging bag 3 introduced into the device main body 11, against the prescription condition input device 50. After receiving this request, the prescription condition input device 50 analyzes the request, specifies prescription condition information related to the request, and transmits the specified prescription condition information to the processing device 12.

The image acquisition unit 23 is connected to the image capturing unit 16 (more precisely, the first camera 16a and the second camera 16b) and acquires, via a network, an image captured by the image capturing unit 16. Here, the image acquired by the image acquisition unit 23 corresponds to image data in specifically, JointPhotographic Experts-Group (JPEG) format, Graphics Interchange Format (GIF) format, PortableNetworkGraphics (PNG) format, Tagged-ImageFile Format (TIFF), or Bitmap Image (BMP) format.

Note that the image acquisition unit 23 acquires an image from the image capturing unit 16 each time the image capturing unit 16 captures an image. More specifically, in the present embodiment, as described above, images are captured a plurality of times (specifically, eight times) separately imaging conditions (for each of imaging conditions) for one packaging bag 1 in which medicines are packaged. Accordingly, the image acquisition unit 23 acquires a plurality of images while changing imaging conditions (that is, eight images for each of imaging conditions) for each of the packaging bags 1 and the medicines packed in the packaging bags 1.

Furthermore, when the packaging bag 1 disposed on the arrangement unit 15 is switched, the image capturing unit 16 newly captures an image under a different imaging condition. Accordingly, the image acquisition unit 23 acquires a plurality of newly captured images with different imaging conditions.

The preprocessing unit 24 performs preprocessing on the image acquired by the image acquisition unit 23 from the image capturing unit 16 (that is, the image data of the verification target medicine). The preprocessing is a process for emphasizing the identification information formed on the surface of the medicine appearing in the image acquired by the image acquisition unit 23.

More specifically, in the present embodiment, as described above, an image is captured a plurality of times (specifically, four times) in various light irradiation directions for the medicine packed in one packaging bag 1. Here, each of the images for each of the light irradiation directions has unevenness in light illuminance occurring on the surface of the medicine appearing in the image. Such uneven illuminance of light has an influence in detecting and specifying identification information formed on the surface of the medicine. Furthermore, the illuminance unevenness of light varies depending on the light irradiation direction. Therefore, using an image captured in each of light irradiation directions, the preprocessing unit 24 performs preprocessing of combining a highlighted portion in relation to the light irradiation direction in the contours (edges) of the identification information appearing in each of the images in order to emphasize the identification information on the surface of the medicine. Alternatively, the preprocessing unit 24 applies the photometric stereo method to the images captured in each of light irradiation directions so as to combine images to highlight the identification information commonly captured in each of the images in consideration of the light irradiation direction of each of the images.

The image that has undergone the above preprocessing is an image from which the illuminance unevenness of light that varies according to the light irradiation direction is eliminated as much as possible and in which the identification information formed on the surface of the medicine appearing in the image is emphasized.

The verification unit 25 performs verification as to whether the number and type of the medicines (that is, the verification target medicines) packed in the packaging bag 1 disposed on the arrangement unit 15 match the quantity and type of the medicines specified from the prescription condition information acquired by the prescription condition information acquisition unit 22.

Figure 9:
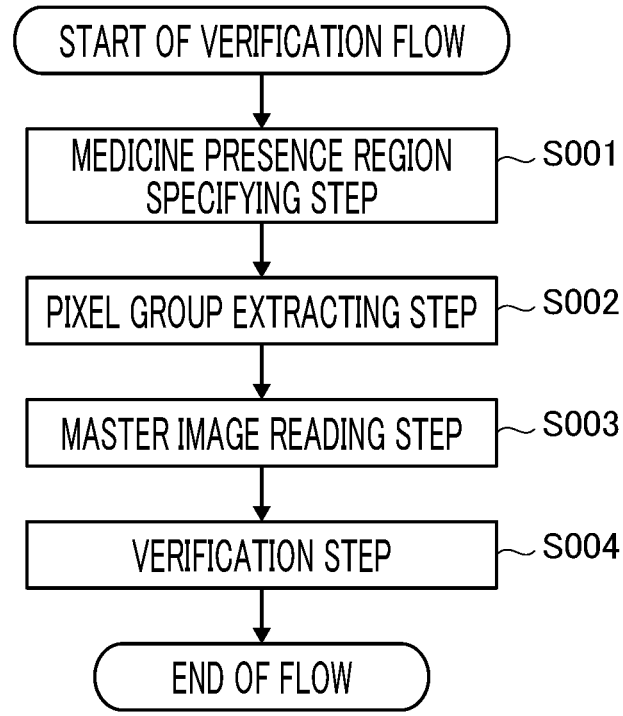
FIG. 9 is a diagram illustrating a general verification flow performed by a verification unit.

The specific procedure of the verification performed by the verification unit 25 will be described with reference to FIG. 9. FIG. 9 is a diagram illustrating a general verification flow performed by the verification unit 25. The verification flow of the verification unit 25, as illustrated in FIG. 9, first performs a step of specifying a region including an image of a verification target medicine from the image on which preprocessing has been performed (S001). Hereinafter, an image on which preprocessing has been performed is referred to as a "preprocessed image", and a region including an image of a medicine in the preprocessed image is referred to as a "medicine presence region".

The medicine presence region specifying step S001 performs a known edge extraction process and a known segmentation process on the preprocessed image to specify a contour of the medicine in the image. Then, a region surrounded by the specified contour is specified as a medicine presence region. In a case where a plurality of medicines are captured in the preprocessed image, the medicine presence regions are specified by the number of medicines.

Figure 10:
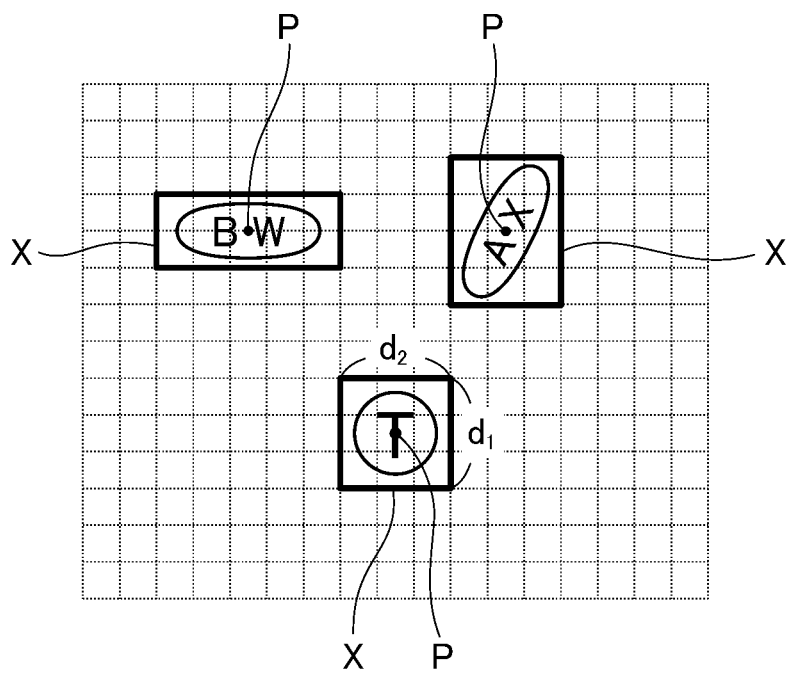
FIG. 10 is a view illustrating a medicine extraction image.

After performing the medicine presence region specifying step S001, the verification unit 25 extracts a pixel group corresponding to the medicine presence region from among the pixel group forming the preprocessed image (S002). As illustrated in FIG. 10, the extracted pixel group forms a rectangle (rectangular region denoted by reference symbol X in FIG. 10) surrounding the medicine presence region.

Hereinafter, the extracted pixel group is referred to as a "medicine extraction image X". In a case where a plurality of medicine presence regions are specified in the medicine presence region specifying step S001, the medicine extraction image X is specified for each of medicine presence regions.

FIG. 10 is a view illustrating the medicine extraction image X. Note that the pixel size (single pixel size with respect to the image) illustrated in FIG. 10 is larger than the actual pixel size for the sake of convenience of illustration.

The pixel group extracting step S002 specifies the size and the position of the medicine extraction image X. Here, the size of the medicine extraction image X is the area of a rectangular pixel group forming the medicine extraction image X and corresponds to the product of lengths d1 and d2 of the two sides illustrated in FIG. 10.

Furthermore, the position of the medicine extraction image X is a coordinate position when the reference position is an origin and the conveyance direction and the intersecting direction are defined as coordinate axis directions. Specifically, this corresponds to an intersecting position of the diagonal lines of the rectangular pixel group forming the medicine extraction image X, namely the coordinates of point P illustrated in FIG. 10. By specifying the position of the medicine extraction image X in this manner, it is possible to specify the imaging position (arrangement position) of the verification target medicine corresponding to the imaging range of the image capturing unit 16 (more precisely, the angle of view of each of the first camera 16*a* and the second camera 16*b*). While the present embodiment is a case where the reference position as the origin is set at the center position of the imaging range of the image capturing unit 16 (more precisely, the first camera 16*a* and the second camera 16*b*), the position is not limited to this and it may be set at any position.

After execution of the pixel group extracting step S002, the verification unit 25 executes a step of specifying the type of medicine to be prescribed from the prescription condition information acquired using the prescription condition information acquisition unit 22 and then reading a master image of the specified type of medicine from the database DB (S003). In this step S003, in a case where a plurality of types of medicines to be prescribed exist, that is, where a plurality of types of medicines are packaged in the packaging bag 1, a master image is read for each of types.

Here, the master image will be described. The master image is an image of a medicine registered corresponding to the type of medicine and is an image registered in advance for the type of medicine specified from the prescription condition information. Furthermore, in the present embodiment, the master image is an image of a medicine captured in a state of being packed in the packaging bag 1. In addition, in a case where verification of a type of medicine has been performed by the verification unit 25 in the past, a captured image of the medicine when a verification result to match the prescription condition is obtained, out of the images (more precisely, medicine extraction images X) of the type of medicine captured in the past by the image capturing unit 16, will be registered as a new master image.

Figures 11, 12:
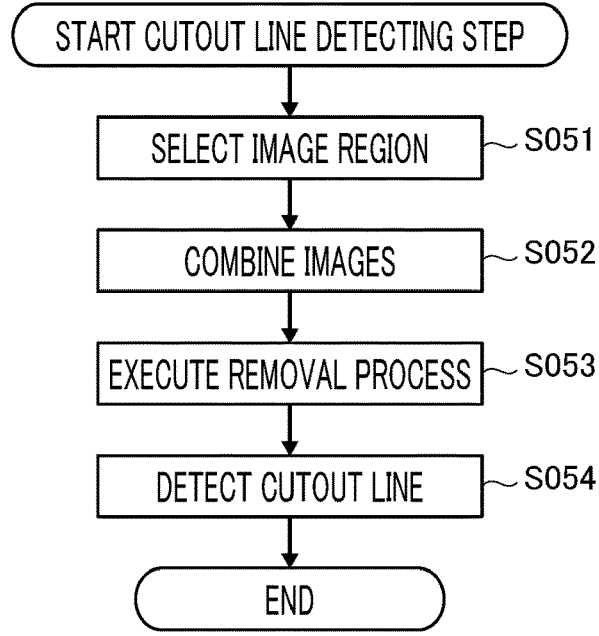
FIG. 11 is a diagram illustrating a database in which master images are registered.
FIG. 12 is a diagram illustrating a flow of a cutout line detecting step.

The database DB will be described. As illustrated in FIG. 11, the database DB is a database in which a master image of each of medicines and a type of the medicine are registered in association with each other. FIG. 11 is a diagram illustrating a database DB in which master images are registered.

In addition to the master image, the database DB includes a medicine name, identification information formed on the surface of the medicine, a plan view size and a thickness as medicine size individually registered in association with the type of the medicine. The information registered in the database DB is not limited to the above information, and information other than the above information may be registered.

In the present embodiment, the database DB is provided in a database server 70 externally provided, and the verification unit 25 communicates with the database server 70 to access the database DB. However, the present invention is not limited to this, and the database DB may be provided in the processing device 12, that is, may be stored in a storage medium in the processing device 12.

After reading the master image from the database DB, the verification unit 25 verifies whether the type of the verification target medicine matches the type of the medicine appearing in the master image (that is, the type of medicine specified from the acquired prescription condition information) using the read master image and the image of the verification target medicine captured by the image capturing unit 16 (more precisely, the medicine extraction image X) (S004). More specifically, the verification step S004 performs template matching between the master image and the medicine extraction image X and then evaluates the similarity between the medicine appearing in the master image and the medicine appearing in the medicine extraction image X (that is, the verification target medicine). Examples of an applicable similarity evaluation method include a known geometric hashing method or a Locally Likely Arrangement Hashing (LLHA) method. Subsequently, in a case where the similarity is a reference value or more, the verification unit 25 verifies that the type of the medicine appearing in the medicine extraction image X matches the type of the medicine appearing in the master image.

In a case where there are a plurality of medicine extraction images X, the similarity is evaluated for each of the medicine extraction images X. In addition, the verification unit 25 counts, for each of types of medicines, the number of images verified to match the type of medicine appearing in the master image among the images appearing in the medicine extraction image X (hereinafter, referred to as medicine type matching number). Subsequently, the verification unit 25 verifies whether the medicine type matching number counted for each of types is the same as the number of prescriptions for each of types specified from the prescription condition information.

The verification is performed by the verification unit 25 using the procedure described above. In addition, when the packaging bag 1 disposed on the arrangement unit 15 is switched (that is, when the verification target medicine changes), the verification is repeated each of times. That is, when the packaging bag 1 disposed on the arrangement unit 15 is switched and an image of the medicine packed in the packaging bag 1 is acquired, verification is performed using the newly acquired image. When the medicines are packaged under the same prescription condition in each of the packaging bags 1 of the continuous packaging bag 3, the master image used in the first verification can be used as it is in the second and subsequent verifications. Accordingly, step S003 of reading a master image from the database DB may be omitted.

With the procedure described above, verification is performed on the medicine packed in each of the packaging bags 1 of the continuous packaging bag 3 (more precisely, the packaging bag 1 other than the empty bag 1A), it is possible to confirm (inspect) whether the medicine is correctly packaged in each of the packaging bags 1 as instructed by the prescription.

The detection unit 27 detects the cutout line 3y (boundary recess) formed at a boundary position between the packaging bags 1 in the continuous packaging bag 3 introduced into the housing 13. The detection of the cutout line 3y by the detection unit 27 is performed in order to define an imaging range in the continuous packaging bag 3 when the verification unit 25 verifies the suitability of the medicine packed in the packaging bag 1.

More specifically, for example, when the image capturing unit 16 is allowed to capture an image of the imaging target portion 3x without detecting the cutout line 3y, an image might be captured in a state where each of the packaging bags 1 in the continuous packaging bag 3 is shifted from a proper position, in some cases. In such a case, the captured image might be an image extending across the cutout line 3y, leading to a possibility that the medicines packaged in each of the two adjacent packaging bags 1 might appear together in one image. For this reason, in the present embodiment, the detection unit 27 detects the cutout line 3y in the continuous packaging bag 3 before verification is performed by the verification unit 25.

Furthermore, in the present embodiment, the detection unit 27 detects the cutout line 3y in the imaging target portion 3x in the continuous packaging bag 3 on the bases of the images with different imaging conditions acquired by the image acquisition unit 23 (in other words, images with different imaging conditions captured by the image capturing unit 16). The specific procedure for detecting the cutout line 3y will be described below in detail.

The removal process execution unit 28 executes a removal process of removing the image of the medicine from the image that is used when the detection unit 27 detects the cutout line 3y. The detection unit 27 detects the cutout line 3y in the imaging target portion 3x on the basis of the image on which the removal process has been performed by the removal process execution unit 28 (that is, the image from which the medicine image has been removed). The details of the removal process will be described below together with the procedure for detecting the cutout line 3y.

«Cutout Line Detection Method»

Next, a method for detecting the cutout line 3y in the present embodiment will be described. Note that the method for detecting the cutout line 3y corresponds to the method for detecting a boundary recess according to the present invention. The basic operation of the medicine verification device 10 including the step of detecting the cutout line 3y described below utilizes the method for detecting a boundary recess of the present invention.

Before describing the method for detecting the cutout line 3y in the present embodiment, a problem related to the conventional detection of the cutout line 3y will be described. In a general method of detecting the cutout line 3y, an image of the imaging target portion 3x is captured by the image capturing unit 16, and the cutout line 3y appearing in the image is detected. At the time of image capturing, the light irradiation unit 17 emits light toward the imaging target portion 3x. When the light emitted by the light irradiation unit 17 reaches the cutout line 3y in the imaging target portion 3x, the light is irregularly reflected at the cutout line 3y. Therefore, the luminance (brightness) in the captured image increases at a portion where the cutout line 3y is formed as illustrated in FIGS. 7A and 7B.

On the other hand, since the medicine is packaged in the packaging bag 1, the portion of the surface of the packaging bag 1 that is located near the cutout line 3$y$ is more raised than the portion where the cutout line 3$y$ is formed in the continuous packaging bag 3. For this reason, as illustrated in FIG. 6, a part of the light emitted by the light irradiation unit 17 toward the imaging target portion 3$x$ is reflected at a portion of the surface of the packaging bag 1 that is raised near the cutout line 3$y$ (a portion with a symbol Rf1 in FIG. 6). The reflected light is captured by the image capturing unit 16. As a result, as illustrated in FIGS. 7A and 7B, a line having a higher luminance than the surroundings appears near the cutout line 3$y$ in the captured image. This leads to a possibility that this line (hereinafter, a false cutout line 3$r$) would be falsely detected as cutout line 3$y$.

As described above, in detection of the cutout line 3$y$ from the image of the imaging target portion 3$x$ captured by the image capturing unit 16, there is a need to avoid false detection of the false cutout line 3$r$. Therefore, in the present embodiment, the cutout line 3$y$ in the imaging target portion 3$x$ in the continuous packaging bag 3 is detected using images captured by the image capturing unit 16 under different imaging conditions. According to the detection method of the present embodiment, it is possible to avoid false detection of the false cutout line 3$r$, leading to accurate detection of the cutout line 3$y$. Hereinafter, the detection procedure of the cutout line 3$y$ will be described with reference to the above-described FIG. 6 and FIGS. 12 to 16.

Figure 13:
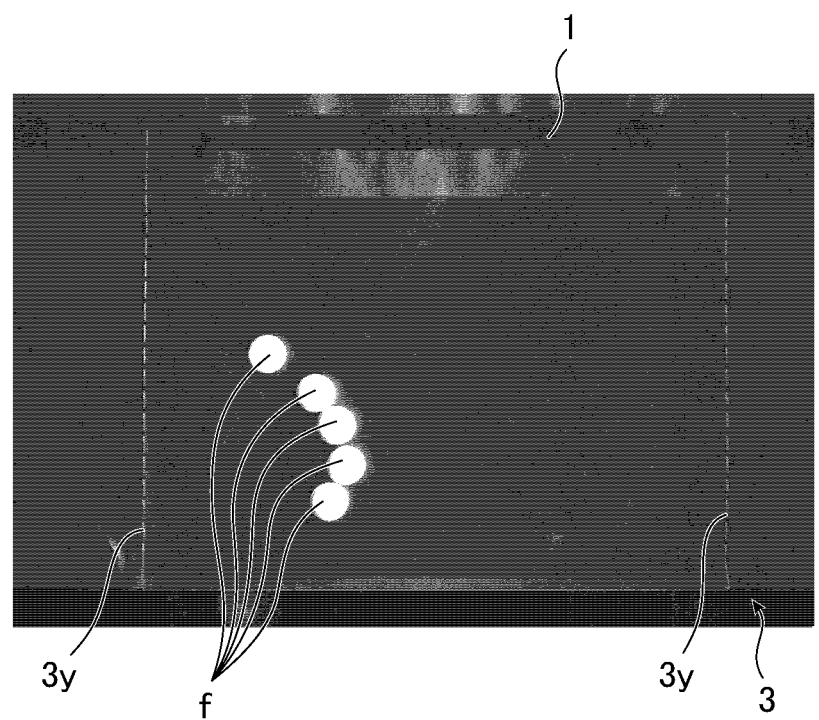
FIG. 13 is an example of a combined image.
Figure 14:
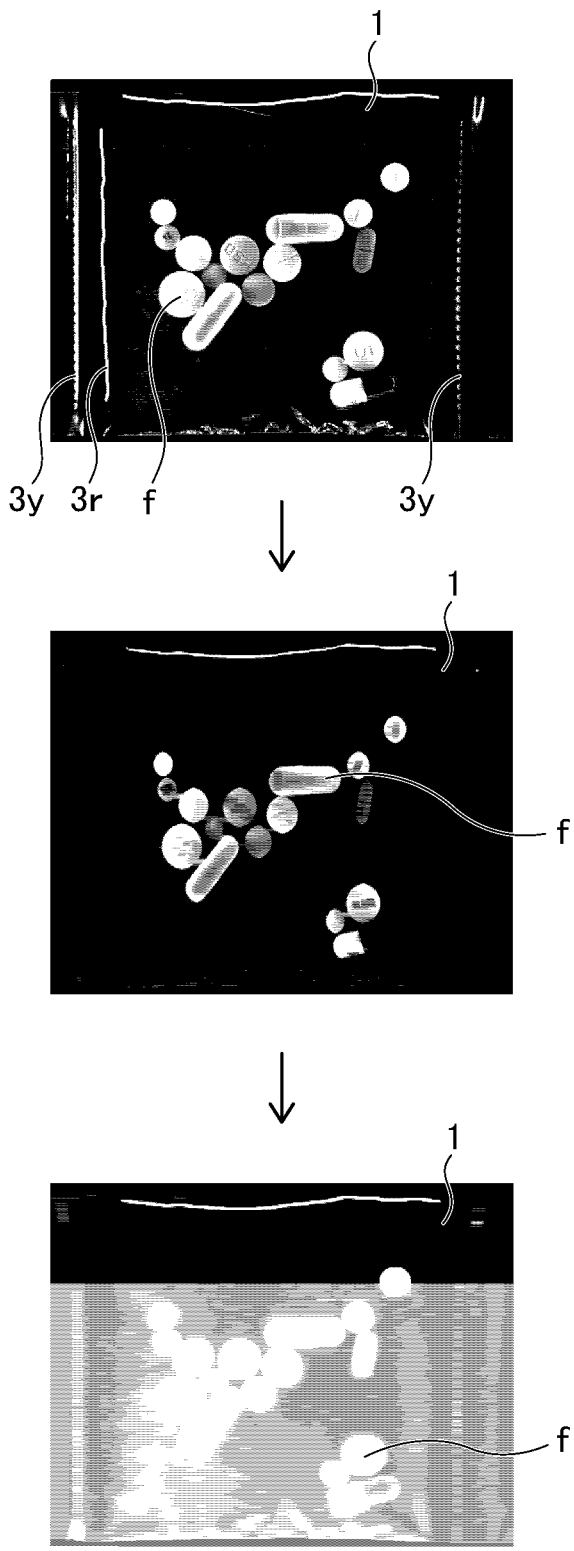
FIG. 14 is a view (images) including a flow of an image contraction/dilation process.
Figure 15:
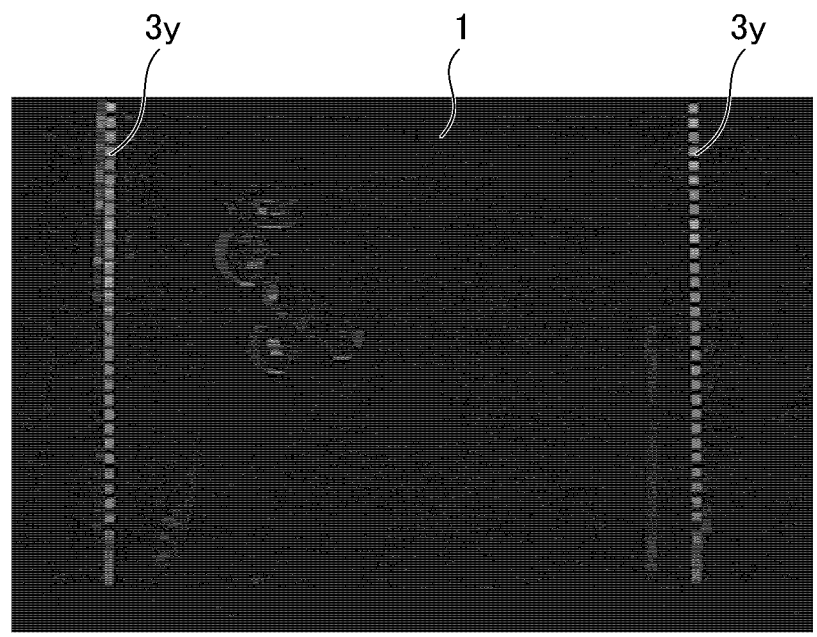
FIG. 15 is an example of an image on which removal process has been performed.
Figure 16:
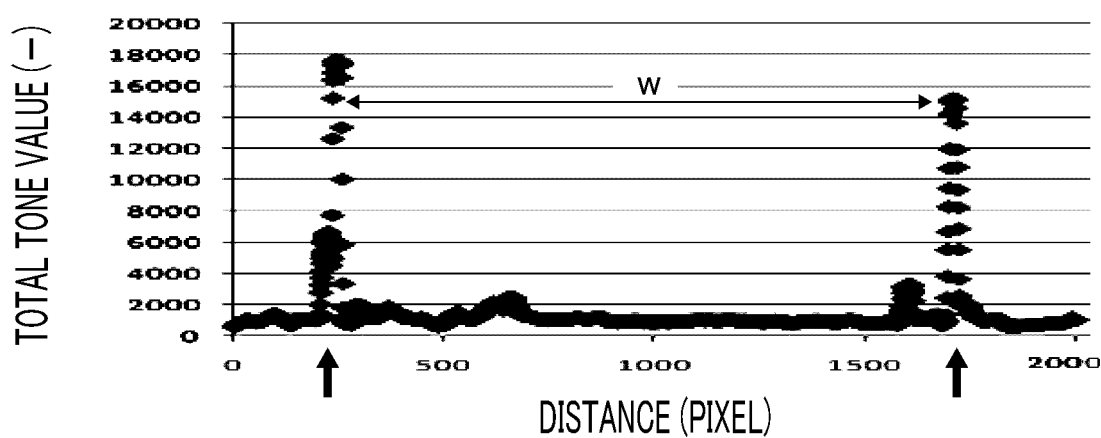
FIG. 16 is a diagram illustrating a correspondence, in an image on which a removal process has been performed, between a distance from an end position of the image and a total tone value.

FIG. 12 is a diagram illustrating a flow of steps of detecting the cutout line 3$y$ by the detection unit 27 (hereinafter, a cutout line detecting step). FIG. 13 is an example of a combined image described below. FIG. 14 is a view (images) including a flow of an image contraction/dilation process. FIG. 15 is an example of an image on which the removal process has been performed by the removal process execution unit 28. FIG. 16 is a diagram illustrating a correspondence, in an image on which a removal process has been performed, between a distance from an end position of the image and a total tone value. The horizontal axis in FIG. 16 represents the distance from the edge position of the image in the conveyance direction (specifically, the end position closer to the upstream side in the conveyance direction) in units of pixels, while the vertical axis represents the total tone values (density) of the pixels located at a same distance.

In the cutout line detecting step, the detection unit 27 detects the cutout line 3$y$ in the imaging target portion 3$x$ using the first image and the second image described above among the images having different imaging conditions captured by the image capturing unit 16. More specifically, the detection unit 27 uses, as the first image, the image of the surface of the imaging target portion 3$x$ captured by the image capturing unit 16 using the first camera 16$a$ while the light irradiation unit 17 performs light emission toward the surface of the imaging target portion 3$x$ using the first light emitting unit 17$a$. Furthermore, the detection unit 27 uses, as the second image, the image of the surface of the imaging target portion 3$x$ captured by the image capturing unit 16 using the first camera 16$a$ while the light irradiation unit 17 performs light emission toward the surface of the imaging target portion 3$x$ using the second light emitting unit 17$b$.

In the cutout line detecting step, the detection unit 27 first selects a certain region individually from the first image and the second image as illustrated in FIG. 12 (S051). More specifically, the detection unit 27 divides the first image into two in a direction corresponding to the conveyance direction (that is, the lateral direction of the image) and selects a portion closer to the downstream side in the conveyance direction in the first image. Note that the portion closer to the downstream side in the conveyance direction in the first image corresponds to a portion in the imaging target portion 3$x$ in which a region farther from the first light emitting unit 17$a$ appears.

Similarly, the detection unit 27 divides the second image into two in the lateral direction of the image and selects a portion of the second image closer to the upstream side in the conveyance direction. Note that the portion closer to the upstream side in the conveyance direction in the second image is a portion in the imaging target portion 3$x$ in which a region farther from the second light emitting unit 17$b$ appears.

The reason why the detection unit 27 selects portions of the first image and the second image each of which is farther from the light emitting unit 17$a$ or 17$b$ used by the light irradiation unit 17 at the time of image capturing is because the false cutout line 3$r$ would not likely to emerge in the selected portions. More specifically, the light irradiation unit 17 emits light toward the imaging target portion 3$x$ in a state where one packaging bag 1 disposed on the arrangement unit 15 and the cutout lines 3$y$ provided on both sides of the packaging bag 1 are located within the imaging target portion 3$x$. In this case, as illustrated in FIG. 6, the light is reflected at the cutout line 3$y$ closer to the light emitting unit 17$a$ or 17$b$ emitting light at that time and at a portion in the vicinity of the cutout line 3$y$ (a portion indicated by the symbol Rf1 in FIG. 6), and then the reflected light is captured by the image capturing unit 16. As a result, in the captured image, the false cutout line 3$r$ is likely to appear in a portion closer to the light emitting unit 17$a$ or 17$b$ that emits light.

In contrast, even when the light is reflected at a raised position (position with a symbol Rf2 in FIG. 6) on the side farther from the light emitting unit 17$a$ or 17$b$ used by the light irradiation unit 17 in the packaging bag 1 described above, the reflected light would not reach the image capturing unit 16 as illustrated in FIG. 6. Therefore, the false cutout line 3$r$ would not be likely to emerge at a portion of the captured image that is farther from the light emitting unit 17$a$ or 17$b$ that emits light. In view of such a property, the detection unit 27 detects the cutout line 3$y$ in the imaging target portion 3$x$ using a portion of each of the first image and the second image that is farther from the light emitting unit 17$a$ or 17$b$ used by the light irradiation unit 17 at the time of capturing the image.

Returning to the description of the cutout line detecting step, the detection unit 27 combines the portions of the first image and the second image selected in the previous step S051 to create a combined image (S052). The combined image includes a conveyance direction downstream half in the first image and a conveyance direction upstream half in the second image. Accordingly, the false cutout line 3$r$ does not appear in the combined image for the reason described above, and the medicine packed in the packaging bag 1 and the cutout line 3$y$ are main objects of the image as illustrated in FIG. 13. Subsequently, the detection unit 27 detects the cutout line 3$y$ in the imaging target portion 3$x$ based on the combined image.

The flow after the creation of the combined image will be specifically described. The removal process execution unit 28 performs a removal process on the combined image (S053). In the present embodiment, the removal process is performed by applying a contraction/dilation technique as an image processing technique. That is, the removal process execution unit 28 executes the removal process of removing an image of the medicine in the combined image by removing a post-contraction-dilation image obtained by applying contraction and dilation on the pixel group constituting the combined image in at least one direction from the image before application of the contraction and dilation.

The flow of the removal process will be described with reference to FIG. 14. Note that FIG. 14 illustrates an image captured by the image capturing unit 16 (more precisely, an image obtained by converting the captured image from a Red Green Blue (RGB) image to a gray scale image) instead of a combined image, for facilitating the procedure of contraction/dilation.

The image in the upper part of FIG. 14 illustrates an image before undergoing contraction and dilation. When the pixel group constituting this image is contracted in a direction corresponding to the conveyance direction (that is, the lateral direction of the image), it is possible to obtain an image (contracted image) in which a line or the like extending in the direction corresponding to the intersecting direction in the image before undergoing contraction and dilation (that is, the vertical direction of the image) has disappeared as illustrated in the image in the middle part of FIG. 14. Here, when individual pixels in the image are converted to black and white binary and when any of the pixels around a target pixel is black, contraction is performed so as to turn the target pixel to black to contract one pixel.

Thereafter, by dilating the pixel group constituting the contracted image in the lateral direction of the image, it is possible to obtain an image (post-contraction-dilation image) in which the medicine and the vertical lines such as the cutout line 3y appearing in the contracted image has returned to the pre-contraction size in the lateral direction as illustrated in the lower part of FIG. 14. Here, when individual pixels in the image are converted to black and white binary and when any of the pixels around a target pixel is white, dilation is performed so as to turn the target pixel to white to dilate one pixel.

In the present embodiment, the contraction and dilation are performed in the direction corresponding to the conveyance direction (that is, the lateral direction of the image). However, the present invention is not limited to this, and contraction and dilation may be performed in the direction corresponding to the intersecting direction (that is, vertical direction of the image) or contraction and dilation may be performed not only in one direction but also in a plurality of directions.

Subsequently, when the post-contraction-dilation image is removed from the pre-contraction-dilation image (in other words, a difference image between the two images is obtained), the medicine image in the pre-contraction-dilation image will be removed. The removal process performed on the combined image according to the above procedure leads to acquisition of a combined image in which only the cutout line 3y remains as illustrated in FIG. 15. Note that the combined image illustrated in FIG. 15 is an image obtained by dilating a pixel group constituting the combined image after the removal process in the lateral direction of the image.

After completion of the removal process, the detection unit 27 detects the cutout line 3y in the imaging target portion 3x based on the combined image after the removal process (that is, the combined image from which the medicine image has been removed) (S054). An example of a method for detecting the cutout line 3y from the combined image after the removal process is a method of specifying the relationship between the position of each of pixels constituting the combined image after the removal process and the tone value (density) so as to detect the cutout line 3y.

More specifically, the detection unit 27 defines a plurality of pixels, which are located at the same distance from the end position of the combined image, from among the pixels constituting the combined image after the removal process, as one pixel column (a column in a vertical direction of the image). Subsequently, the detection unit 27 totals the tone values of individual pixels in the pixel column by the number of pixels in the pixel column. By calculating this total value (hereinafter, total tone value) by the number of pixel columns existing in the combined image after the removal process, it is possible to specify correspondence between the position of the pixel column and the total tone value as illustrated in FIG. 16.

Based on the specified correspondence, the detection unit 27 specifies a pixel column whose total tone value is higher than in the surrounding pixel columns and whose total tone value exceeds a threshold. For example, in the case illustrated in FIG. 16, a pixel column whose distance from the end position of the combined image is the distance indicated by the arrow in FIG. 16 is specified. Accordingly, the detection unit 27 detects, as the cutout line 3y, a portion corresponding to the specified pixel column in the imaging target portion 3x. Incidentally, the detection unit 27 detects two cutout lines 3y in the imaging target portion 3x from an image (more precisely, a combined image) of one imaging target portion 3x.

Furthermore, the detection unit 27 calculates an interval (distance indicated by a symbol w in FIG. 16) between the two detected cutout lines 3y and transmits the calculation result to the control unit 21. The control unit 21 controls the conveyance unit 14 based on the calculation result of the interval between the cutout lines 3y transmitted from the detection unit 27. More specifically, the control unit 21 sets the conveyance amount in one conveyance operation to an amount corresponding to the calculation result of the interval between the cutout lines 3y.

Figure 17:
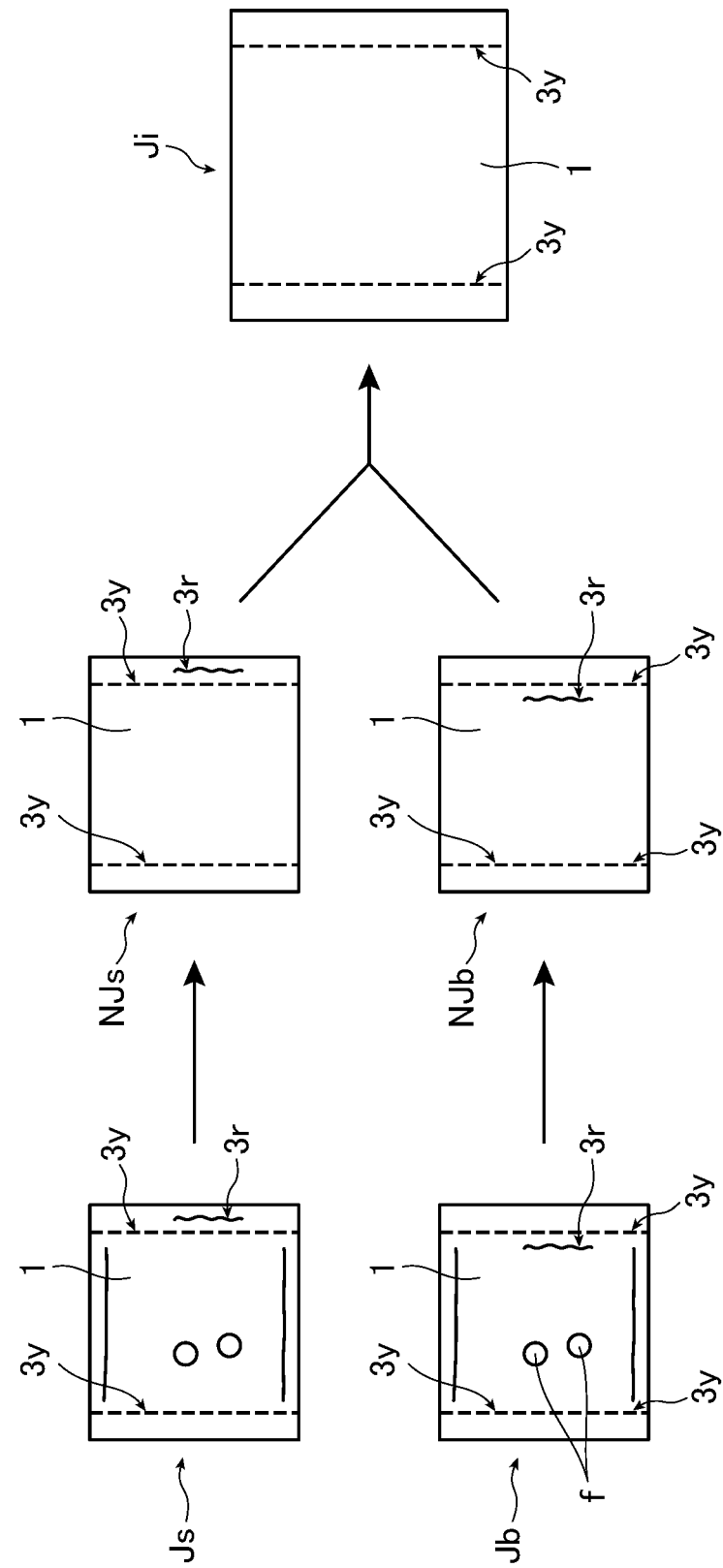
FIG. 17 is a view illustrating a modification of a procedure for detecting a cutout line.

While an example of the procedure for detecting the cutout line 3y has been described above, the cutout line 3y may be detected by a procedure other than the procedure described above. Hereinafter, a modification of the procedure for detecting the cutout line 3y will be described with reference to FIG. 17. FIG. 17 is a view illustrating a modification of the procedure for detecting the cutout line 3y.

In the cutout line detecting step according to the modification, the detection unit 27 detects the cutout line 3y in the imaging target portion 3x using an image captured by the first camera 16a of the image capturing unit 16 (hereinafter, an upper surface image Js) and an image captured by the second camera 16b of the image capturing unit 16 (hereinafter, a lower surface image Jb) out of the images having different capturing conditions captured by the image capturing unit 16. Here, the upper surface image Js and the lower surface image Jb used by the detection unit 27 are images captured while the light irradiation unit 17 is emitting light from the same light emitting unit 17a, 17b, 17c, or 17d.

As illustrated in FIG. 17, in addition to the medicine f and the cutout line 3y, the false cutout line 3r emerges in the upper surface image Js and the lower surface image Jb at the end closer to the light emitting unit that emitted light at the time of image capturing. Comparing the upper surface image Js and the lower surface image Jb, as illustrated in FIG. 17, the cutout line 3y is imaged at the same position both in the upper surface image Js and the lower surface image Jb, whereas the false cutout lines 3r are imaged at mutually different positions. This is because the irradiation light from the light irradiation unit 17 is reflected at different positions between the upper surface and the lower surface of the packaging bag 1.

In the cutout line detecting step according to the modification, as illustrated in FIG. 17, first, the removal process execution unit 28 performs the removal process on the upper surface image Js and the lower surface image Jb in the procedure similar to the description above. That is, the removal process execution unit 28 performs the removal process by applying contraction and dilation on the pixel group constituting each of the upper surface image Js and the lower surface image Jb captured by the image capturing unit 16 in the direction corresponding to the conveyance direction (that is, the lateral direction of the image). Thereafter, the removal process execution unit 28 removes the post-contraction-dilation image obtained by contracting and dilating each of images, from the pre-contraction-dilation image. This process results in the acquisition of images in which the image of the medicine f is removed from each of the upper surface image Js and the lower surface image Jb, that is, a removal-processed upper surface image NJs and a removal-processed lower surface image NJb.

As illustrated in FIG. 17, the removal-processed upper surface image NJs and the removal-processed lower surface image NJb each include vertical lines along a direction corresponding to the intersecting direction (that is, the vertical direction of the image), specifically, the cutout line 3y and the false cutout line 3r.

After performing the removal process, the detection unit 27 specifies a candidate for the cutout line 3y appearing in the image captured by the first camera 16a (more precisely, the removal-processed upper surface image NJs), and specifies a candidate for the cutout line 3y appearing in the image captured by the second camera 16b (more precisely, the removal-processed lower surface image NJb). Here, the candidate for the cutout line 3y is a vertical line appearing in each of the removal-processed upper surface image NJs and the removal-processed lower surface image NJb, and specifically, the true cutout line 3y and the false cutout line 3r.

Thereafter, the detection unit 27 specifies a candidate for the cutout line 3y appearing both in the image captured by the first camera 16a (more precisely, the removal-processed upper surface image NJs) and in the image captured by the second camera 16b (more precisely, the removal-processed lower surface image NJb). Subsequently, the detection unit 27 detects the specified candidate for the cutout line 3y as the cutout line 3y in the imaging target portion 3x.

More specifically, the detection unit 27 specifies a vertical line appearing both in the removal-processed upper surface image NJs and the removal-processed lower surface image NJb and then generates an integrated image Ji that reflects the result of the specification. The integrated image Ji is an image that includes only images of the vertical lines appearing both in the removal-processed upper surface image NJs and the removal-processed lower surface image NJb. Here, the vertical lines illustrated in the integrated image Ji are cutout lines 3y as illustrated in FIG. 17. Therefore, the detection unit 27 detects the vertical line appearing in the integrated image Ji as the cutout line 3y in the imaging target portion 3x. For detecting the vertical line (that is, the cutout line 3y) in the integrated image Ji, it is possible to utilize a method that uses the above-described correspondence between the position of each of pixel columns in the image and the total tone value in each of the pixel columns (refer to FIG. 16).

«Basic Operation of Medicine Verification Device»

Figure 18:
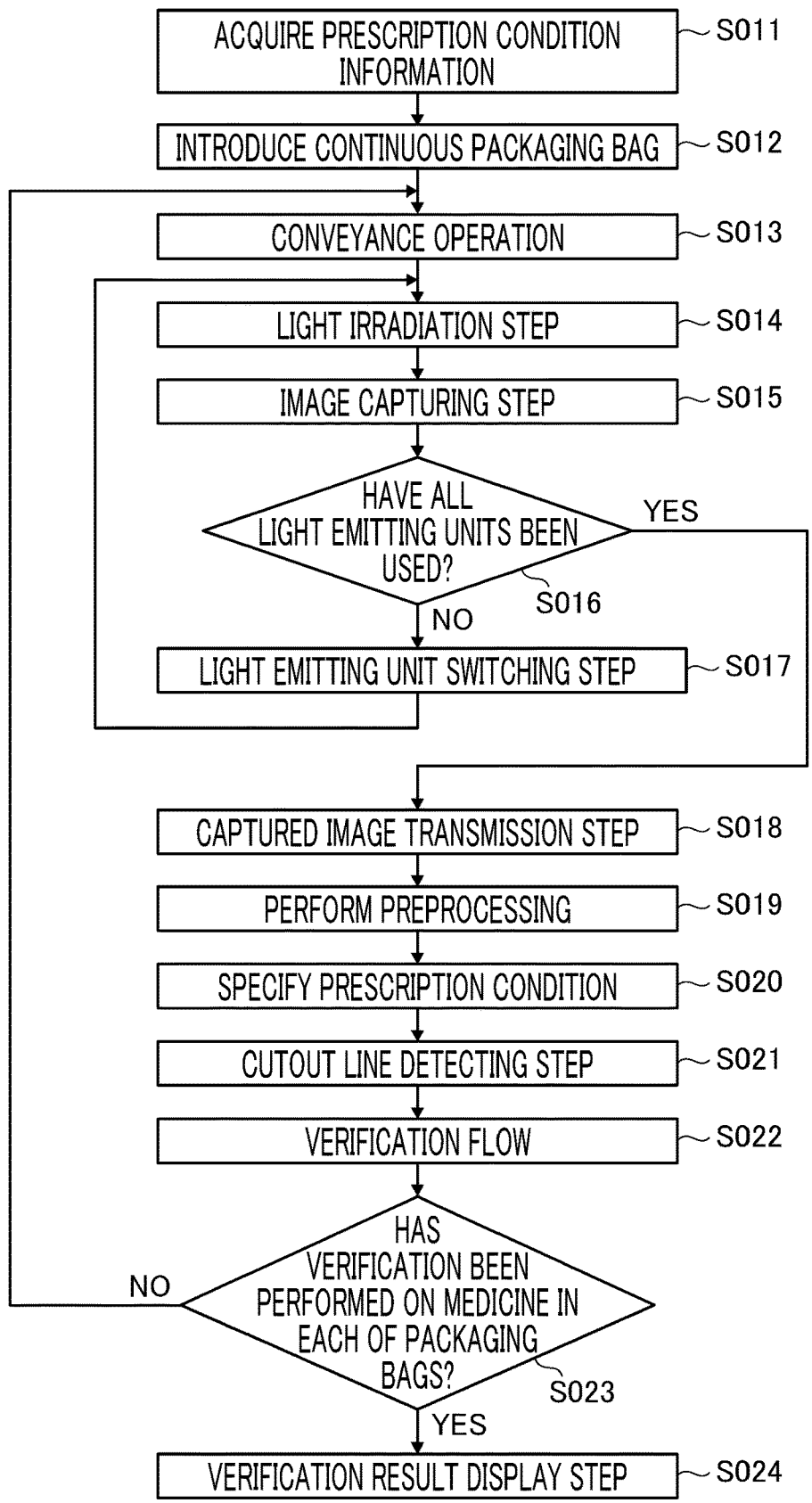
FIG. 18 is a diagram illustrating a flow of a basic operation of the medicine verification device according to one embodiment of the present invention.

Next, basic operation of the medicine verification device 10 will be described with reference to FIG. 18. FIG. 18 is a diagram illustrating a flow of basic operation of the medicine verification device 10.

First, after completion of the input of the prescription condition information in the prescription input operation, the prescription condition information acquisition unit 22 of the processing device 12 communicates with the prescription condition input device 50 and acquires the prescription condition information indicating the input prescription condition (S011).

Meanwhile, after the automatic packaging operation is performed by the packaging machine 60 in accordance with the input prescription condition (in other words, the prescription condition indicated by the prescription condition information acquired by the prescription condition information acquisition unit 22), the continuous packaging bag 3 having a strip-like shape including the continuously connected packaging bags 1 each of which contains the medicine is created. The continuous packaging bag 3 is introduced into the device main body 11 by the introduction part 13a formed in the housing 13 of the device main body 11 (S012).

After the continuous packaging bag 3 is introduced into the device main body 11, the conveyance operation by the conveyance unit 14 is intermittently repeated (S013). In each of conveyance operations, the continuous packaging bag 3 is conveyed by a predetermined amount to the downstream side in the conveyance direction. When the continuous packaging bag 3 is conveyed to the downstream side in the conveyance direction, one of the packaging bags 1 among the continuous packaging bag 3 is eventually disposed on the arrangement unit 15. Each time the conveyance operation is performed, the packaging bag 1 disposed on the arrangement unit 15 among the continuous packaging bag 3 is switched.

During a period between conveyance operations (that is, during stoppage of the conveyance of the continuous packaging bag 3), the light irradiation unit 17 applies light to the medicine packed in the packaging bag 1 disposed on the arrangement unit 15 (S014). In this state, using each of cameras, namely, the first camera 16a and the second camera 16b, the image capturing unit 16 captures an image (that is, a verification target medicine) packed in the packaging bag 1 disposed on the arrangement unit 15 (S015).

The light irradiation step S014 by the light irradiation unit 17 will be described in detail. The light irradiation unit 17 emits light from one of the four light emitting units 17a, 17b, 17c, and 17d disposed around the arrangement unit 15, switches the light emitting units sequentially (S016 and S017), and then emits light again from the newly switched light emitting unit 17a, 17b, 17c, or 17d. That is, the light irradiation unit 17 sequentially switches the light irradiation directions and applies light from each of directions. Subsequently, the image capturing unit 16 captures an image of the verification target medicine for each of light irradiation directions. This enables a total of eight images (the number of cameras×the number of light irradiation directions) to be captured for the medicine packed in the packaging bag 1 disposed on the arrangement unit 15.

The light irradiation step S014, the image capturing step S015, and the light emitting unit switching step S017 described above are repeatedly performed every time the packaging bag 1 disposed on the arrangement unit 15 is switched together with the conveyance operation.

The captured image is transmitted to the image acquisition unit 23 of the processing device 12 as needed (S018). Thereafter, preprocessing is performed by the preprocessing unit 24 of the processing device 12 on the image acquired by the image acquisition unit 23 (S019). This generates a preprocessed image that emphasizes edges of the identification information formed by engraving on the surface of the medicine.

Meanwhile, the verification unit 25 of the processing device 12 specifies a prescription condition for the medicine (that is, the verification target medicine) appearing in the preprocessed image (S020). Specifically, based on the prescription condition information acquired in S011, the verification unit 25 specifies the prescription conditions set for the medicine packaged in each of the packaging bags 1 in the continuous packaging bag 3 (specifically, the type and the number of medicine for each of types).

Furthermore, the detection unit 27 of the processing device 12 performs a cutout line detecting step using an image having a different imaging condition acquired by the image acquisition unit 23 (in other words, an image of the imaging target portion 3x captured by the image capturing unit 16 the imaging condition) (S021). More specifically, the detection unit 27 detects two cutout lines 3y in the imaging target portion 3x using the above-described procedure. Here, in a case where two cutout lines 3y are detected, this means one packaging bag 1 in the continuous packaging bag 3 is correctly disposed on the arrangement unit 15. Conversely, in a case where two cutout lines 3y are not detected, for example, where only one cutout line 3y is detected because the two packaging bags 1 are disposed across the arrangement unit 15, the conveyance unit 14 slightly conveys the continuous packaging bag 3 to adjust the position of the continuous packaging bag 3, and thereafter the detection unit 27 performs the cutout line detecting step again. The conveyance operation for position adjustment by the conveyance unit 14 and the cutout line detecting step are repeated until the detection unit 27 detects the two cutout lines 3y in the imaging target portion 3x.

After detecting the two cutout lines 3y in the imaging target portion 3x, the detection unit 27 calculates an interval between the cutout lines 3y and transmits the calculation result to the control unit 21. The control unit 21 controls the conveyance unit 14 to convey the continuous packaging bag 3 by a conveyance amount corresponding to the calculated value of the interval between the cutout lines 3y in the subsequent conveyance operation of the conveyance unit 14. This enables the packaging bags 1 in the continuous packaging bag 3 to be correctly disposed one by one on the arrangement unit 15 after execution of individual conveyance operations.

In addition, while the conveyance unit 14 is stopped, the verification unit 25 verifies whether the medicine packaged in each of the packaging bags 1 in the continuous packaging bag 3 is correctly packaged as instructed in the prescription condition using the procedure of the verification flow described above (S022). In the verification flow, the verification unit 25 accesses the database DB of the database server 70 and reads the master image corresponding to the prescription condition (specifically, the type of medicine) specified in the previous step S020. Subsequently, the verification unit 25 verifies whether the type and the number of medicines packed in the packaging bag 1 disposed on the arrangement unit 15 is as instructed in the prescription condition using the preprocessed image and the master image.

The above-described series of steps S013 to S022 from the conveyance operation to the verification flow is repeatedly executed every time the packaging bag 1 disposed on the arrangement unit 15 is switched until completion of the verification on the medicines in each of the packaging bags 1 in the continuous packaging bag 3 (S023).

In the flow illustrated in FIG. 18, although the cutout line detecting step S021 is repeatedly performed every time the packaging bag 1 disposed on the arrangement unit 15 is switched, the cutout line detecting step S021 may be performed only for the first time and may be omitted in subsequent times.

The verification unit 25 performs the above-described verification with the medicine packaged in each of the packaging bags 1 in the continuous packaging bag 3 as a verification target. After completion of all verifications, the verification unit 25 displays character information indicating the result (verification result) on a display (S024).

The verification result to be displayed on the display may be displayed in any manner as long as it is possible to clearly grasp which packaging bag 1 in the continuous packaging bag 3 is the verification result for the medicine packed in the packaging bag 1. Accordingly, the verification results may be displayed by switching for each of the packaging bags, or verification result for each of the packaging bags 1 in the continuous packaging bag 3 may be displayed collectively in association with the position or order of the packaging bag 1.

Thereafter, the conveyance operation of the conveyance unit 14 allows the continuous packaging bag 3 to reach the discharge part of the housing 13 of the device main body 11, and the packaging bag 1 at the end of the continuous packaging bag 3 (the packaging bag 1 located most upstream in the conveyance direction) is discharged out of the housing 13, and the basic operation of the medicine verification device 10 is completed at this point.

«Effectiveness of the Medicine Verification Device According to the Present Embodiment»

As described above, the medicine verification device 10 and the boundary recess detection method (specifically, the method for detecting the cutout line 3y) according to the present embodiment are adapted to detect the cutout line 3y in the imaging target portion 3x using an image of the imaging target portion 3x captured by the image capturing unit 16 while changing the imaging conditions. This makes it possible to appropriately detect the position of the cutout line 3y formed in the continuous packaging bag 3. As a result, in cases where the verification (inspection) of the suitability of medicines is individually performed for each of the packaging bags 1 of the continuous packaging bag 3, it is possible to properly define the imaging region in the continuous packaging bag 3. In this regard, the medicine verification device and the boundary recess detection method of the present invention have effects further advantageous than in the techniques described in Patent Literatures 1 to 4.

More specifically, as described in the section of the Background Art, the cutout line 3y is relatively small and easily flattened. Therefore, the cutout line 3y in the image cannot be clearly confirmed and not easily detected. In addition, in the case of detecting the cutout line 3y by capturing an image near the cutout line 3y while emitting light toward the position where the cutout line 3y is formed in the continuous packaging bag 3, there is a possibility that the false cutout line 3r appears in the vicinity of the cutout line 3y and this false cutout line 3r might be falsely recognized as the cutout line 3y as described above. To handle this, the technique described in Patent Literatures 1 to 4 do not directly detect the cutout line 3y but indirectly detect the cutout line 3y by detecting a portion near the cutout line 3y or a candidate for the cutout line 3y or the like.

More particularly, the technique described in Patent Literature 1 uses the difference in the scattering property at light transmission between the heat-sealed portion and the non-sealed portion in the sachet sheet so as to highlight the background image on the illumination side only at the package end, thereby detecting the package end.

The technique described in Patent Literature 2 determines the combination in which the derived value of the length of the sachet that is the inspection target is close to the prescribed value, among the combination candidates of the upstream boundary candidate and the downstream boundary candidate, as the boundary position located on the upstream side and the downstream side of the sachet as an inspection target.

The techniques described in Patent Literatures 3 and 4 recognize an edge region from an interval between vertical edges longer than a predetermined length and then determine the center of the edge region as a boundary position between the vertical seal portions.

In contrast, the medicine verification device 10 according to the present embodiment captures an image of the imaging target portion 3x of the continuous packaging bag 3 in which the image of the cutout line 3y is located a plurality of times while changing the imaging conditions. By using a plurality of captured images that have been captured under different imaging conditions, it is possible to remove the false cutout line 3r from the image. This makes it possible to directly detect the cutout line 3y from the captured image. Furthermore, in the case of using the technique described in Patent Literature 1, it would be necessary to have a light scattering property difference between the heat-sealed portion and the non-sealed portion. Fortunately, however, the medicine verification device 10 according to the present embodiment can also be applicable to a continuous packaging bag 3 that does not have such characteristic.

Furthermore, a prescribed value of the length of the sachet as an inspection target is required in order to use the technique described in Patent Literature 2, and therefore, the technique cannot be used when the prescribed value is unknown. In addition, there are cases, in the technique of Patent Literature 2, where there are a plurality of combinations having derived values of the length of the sachet as an inspection target close to the prescribed value, among the candidate combinations of the upstream boundary candidate and the downstream boundary candidate. In such a case, it is difficult to decide the boundary position from among the boundary candidates. In contrast, the medicine verification device 10 according to the present embodiment would not need the above-described prescribed value. In addition, since the boundary candidates are limited (not too many), it is possible to detect the cutout line 3y with higher convenience and accuracy.

Furthermore, the techniques described in Patent Literatures 3 and 4 specify the boundary positions under the premise that the package boundary position exists at the center position of the edge region, and thus, it would be difficult to accurately specify the position of the cutout line in a case where the cutout line is provided at a position deviated from the center of the edge region, for example. In comparison, the medicine verification device 10 according to the present embodiment directly detects the cutout line 3y as described above, making it possible to detect the cutout line 3y with higher accuracy.

OTHER EMBODIMENTS

While the medicine verification device and the boundary recess detection method of the present invention have been described above with reference to a specific example, the above embodiments are merely an example, and other embodiments are conceivable. For example, the above embodiment has described a case where a plurality of medicines are packaged in each of the packaging bags 1 (excluding the empty bag 1A) in the continuous packaging bag 3. However, the present invention is not limited to this. The number of medicines packaged in each of the packaging bags 1 can be set to any number and may be only one, or may be two or more.

Furthermore, the above-described embodiment has described an exemplary case of the medicine verification device 10 used to verify the suitability of the medicines packaged in the packaging bag 1 when the pharmacist prescribes the medicines to patients. However, the use of the medicine verification device 10 is not limited to the above-described use. The medicine verification device 10 may be utilized for the purpose of grasping the type and quantity (more precisely, the quantity of each of types) of the medicines by operators in a facility like a hospital when they are brought by a patient in the packaging bag 1 when admitted to the facility.

What is claimed is:
1. A medicine verification device comprising:
a detection unit that detects a boundary recess formed at a boundary position between a plurality of packaging bags each of which packs a medicine and is connected to form a continuous packaging bag having a strip-like shape; and
an image capturing unit that captures an image of a surface of an imaging target portion on which at least the boundary recess is located a plurality of times while imaging conditions are changed in a state where light is emitted toward the surface of the imaging target portion in the continuous packaging bag,
wherein the detection unit detects the boundary recess in the imaging target portion on the basis of the plurality of images captured by the image capturing unit under the imaging conditions changed.
2. The medicine verification device according to claim 1, further comprising
a light irradiation unit that emits light toward the surface of the imaging target portion when the image capturing unit captures an image,
wherein the light irradiation unit includes a first light emitting unit and a second light emitting unit that emit light in mutually opposite directions in a longitudinal direction of the continuous packaging bag and emits light diagonally toward the surface of the imaging target portion,
the image capturing unit captures an image in a state where the capturing target portion is located between the first light emitting unit and the second light emitting unit in the longitudinal direction, and
the light irradiation unit changes a light emitting unit used at the time of light emission out of the first light emitting unit and the second light emitting unit when changing the imaging conditions.

3. The medicine verification device according to claim 2, wherein a medicine is packaged in the packaging bag of the continuous packaging bag, and
the image capturing unit captures an image of a surface of the imaging target portion in which at least an end of the packaging bag in which the medicine is packaged and the boundary recess adjacent to the end are located, a plurality of times under the imaging conditions changed.

4. The medicine verification device according to claim 2, wherein the image capturing unit captures a first image of the surface of the imaging target portion while the light irradiation unit emits light toward the surface of the imaging target portion using the first light emitting unit and captures a second image of the surface of the imaging target portion while the light irradiation unit emits light toward the surface of the imaging target portion using the second light emitting unit, and
the detection unit detects the boundary recess in the imaging target portion using the first image and the second image.

5. The medicine verification device according to claim 4, wherein a medicine is packaged in the packaging bag of the continuous packaging bag, and
the image capturing unit captures an image of a surface of the imaging target portion in which at least an end of the packaging bag in which the medicine is packaged and the boundary recess adjacent to the end are located, a plurality of times under the imaging conditions changed.

6. The medicine verification device according to claim 4, wherein the light emission of the second light emitting unit is stopped during the light emission performed by the light irradiation unit toward the surface of the imaging target portion using the first light emitting unit, and
the light emission of the first light emitting unit is stopped during the light emission performed by the light irradiation unit toward the surface of the imaging target portion using the second light emitting unit.

7. The medicine verification device according to claim 6, wherein a medicine is packaged in the packaging bag of the continuous packaging bag, and
the image capturing unit captures an image of a surface of the imaging target portion in which at least an end of the packaging bag in which the medicine is packaged and the boundary recess adjacent to the end are located, a plurality of times under the imaging conditions changed.

8. The medicine verification device according to claim 6, wherein the detection unit combines a portion in the first image including an image of a region on a side farther from the first light emitting unit out of the imaging target portion and a portion in the second image including an image of a region on a side farther from the second light emitting unit out of the imaging target portion to create a combined image, and the detection unit detects the boundary recess in the imaging target portion on the basis of the combined image.

9. The medicine verification device according to claim 8, wherein a medicine is packaged in the packaging bag of the continuous packaging bag, and
the image capturing unit captures an image of a surface of the imaging target portion in which at least an end of the packaging bag in which the medicine is packaged and the boundary recess adjacent to the end are located, a plurality of times under the imaging conditions changed.

10. The medicine verification device according to claim 1, wherein the image capturing unit includes a first camera and a second camera that images the imaging target portion from mutually opposite directions in a thickness direction of the continuous packaging bag,
the first camera captures an image of one surface of the imaging target portion in the thickness direction,
the second camera captures an image of another surface of the imaging target portion located on the opposite side to the one surface in the thickness direction, and
the detection unit detects the boundary recess in the imaging target portion on the basis of an image captured by the first camera and an image captured by the second camera.

11. The medicine verification device according to claim 10,
wherein a medicine is packaged in the packaging bag of the continuous packaging bag, and
the image capturing unit captures an image of a surface of the imaging target portion in which at least an end of the packaging bag in which the medicine is packaged and the boundary recess adjacent to the end are located, a plurality of times under the imaging conditions changed.

12. The medicine verification device according to claim 10, wherein the detection unit specifies a candidate for the boundary recess appearing in the image captured by the first camera and specifies a candidate for the boundary recess appearing in the image captured by the second camera, and thereafter, the detection unit detects the candidate for the boundary recess appearing in both the image captured by the first camera and the image captured by the second camera, as the boundary recess in the imaging target portion.

13. The medicine verification device according to claim 12,
wherein a medicine is packaged in the packaging bag of the continuous packaging bag, and
the image capturing unit captures an image of a surface of the imaging target portion in which at least an end of the packaging bag in which the medicine is packaged and the boundary recess adjacent to the end are located, a plurality of times under the imaging conditions changed.

14. The medicine verification device according to claim 1, wherein a medicine is packaged in the packaging bag of the continuous packaging bag, and
the image capturing unit captures an image of a surface of the imaging target portion in which at least an end of the packaging bag in which the medicine is packaged and the boundary recess adjacent to the end are located, a plurality of times under the imaging conditions changed.

15. The medicine verification device according to claim 14,
wherein the packaging bag is light transmissive,
the image capturing unit captures an image of a surface of the imaging target portion in which at least a portion covering the medicine, the end, and the boundary recess adjacent to the end are located, out of the packaging bag in which the medicine is packaged, a plurality of times under the imaging conditions changed, and
the medicine verification device further comprises a removal process execution unit that performs, on each of the plurality of images captured under different imaging conditions, a removal process for removing an image of a medicine in each of the plurality of images.

16. The medicine verification device according to claim 15, wherein the removal process execution unit executes the removal process of removing the image of the medicine in the image by removing a post-contraction-dilation image obtained by applying contraction and dilation on a pixel group constituting the image captured by the image capturing unit in at least one direction from an image before application of the contraction and dilation.

17. The medicine verification device according to claim 1, wherein the boundary recess is a cutout line formed by a dashed linear groove formed from one end to the other end of the continuous packaging bag in a lateral width direction of the continuous packaging bag.

18. A boundary recess detection method being a method of detecting a boundary recess formed at a boundary position between a plurality of packaging bags each of which packs a medicine and is connected to form a continuous packaging bag having a strip-like shape, the method comprising:
- a step of capturing an image of a surface of an imaging target portion on which at least the boundary recess is located a plurality of times while imaging conditions are changed in a state where light is emitted toward the surface of the imaging target portion in the continuous packaging bag; and
- a step of detecting the boundary recess in the imaging target portion on the basis of the plurality of images captured under the imaging conditions changed.

* * * * *